US012755834B2

(12) United States Patent
Thomas et al.

(10) Patent No.: US 12,755,834 B2
(45) Date of Patent: Oct. 6, 2026

(54) MONITORING, PREDICTING AND ALERTING FOR CENSUS PERIODS IN MEDICAL INPATIENT UNITS

(71) Applicant: GE Precision Healthcare LLC, Waukesha, WI (US)

(72) Inventors: Bex George Thomas, Laguna Nigel, CA (US); Vijay K. Veeraghattam, Carpentersville, IL (US); Hong Yang, Hoffman Estates, IL (US); Gregory Peter Betman, Chicago, IL (US)

(73) Assignee: GE Precision Healthcare LLC, Waukesha, WI (US)

( * ) Notice: Subject to any disclaimer, the term of this patent is extended or adjusted under 35 U.S.C. 154(b) by 9 days.

(21) Appl. No.: 19/005,832

(22) Filed: Dec. 30, 2024

(65) Prior Publication Data

US 2025/0132026 A1 Apr. 24, 2025

Related U.S. Application Data

(63) Continuation of application No. 17/341,949, filed on Jun. 8, 2021, now Pat. No. 12,224,058, which is a (Continued)

(51) Int. Cl.
*G16H 40/20* (2018.01)
*G06F 16/901* (2019.01)
(Continued)

(52) U.S. Cl.
CPC ......... *G16H 40/20* (2018.01); *G06F 16/9024* (2019.01); *G06F 17/18* (2013.01); (Continued)

(58) Field of Classification Search
CPC ............................... G16H 40/20; G16H 80/00
See application file for complete search history.

(56) References Cited

U.S. PATENT DOCUMENTS

2010/0228565 A1* 9/2010 Rosow .................... G16H 40/20 705/2
2011/0087502 A1* 4/2011 Yelton .................... G16H 10/60 705/2

FOREIGN PATENT DOCUMENTS

WO WO-2018112185 A1 * 6/2018 ............ G16H 40/20

OTHER PUBLICATIONS

Tan, Kar Way, et al. "Data-driven decision-support for process improvement through predictions of bed occupancy rates." 2019 IEEE 15th International Conference on Automation Science and Engineering (CASE). IEEE, 2019. (Year: 2019).*

* cited by examiner

*Primary Examiner* — Constantine Siozopoulos

(57) ABSTRACT

Systems and techniques for monitoring, predicting and/or alerting for census periods in medical inpatient units are presented. A system can include a grouping component that defines a group of beds at a medical facility based on at least one grouping factor, and a group stability component that determines a measure of occupancy variability for the group based on historical census data for respective beds in the group. The system can further include a model selection component that selects one or more census forecasting models for the group based on the measure of occupancy variability, and a patient census component that applies the one or more census forecasting models to current patient flow data for the medical facility to forecast an expected occupancy level for the group during one or more future periods of time.

18 Claims, 18 Drawing Sheets

Related U.S. Application Data continuation-in-part of application No. 16/366,247, filed on Mar. 27, 2019, now Pat. No. 11,043,289.

(51) Int. Cl.

| | |
|---|---|
| ***G06F 17/18*** | (2006.01) |
| ***G06N 5/04*** | (2023.01) |
| ***G06N 20/00*** | (2019.01) |
| ***G06Q 10/04*** | (2023.01) |
| ***G06Q 10/067*** | (2023.01) |
| ***G16H 10/60*** | (2018.01) |
| ***G16H 50/70*** | (2018.01) |

(52) U.S. Cl.

CPC ............... *G06N 5/04* (2013.01); *G06N 20/00* (2019.01); *G06Q 10/04* (2013.01); *G06Q 10/067* (2013.01); *G16H 10/60* (2018.01); *G16H 50/70* (2018.01)

MONITORING, PREDICTING AND ALERTING FOR CENSUS PERIODS IN MEDICAL INPATIENT UNITS

CROSS-REFERENCE TO RELATED APPLICATION

This application is a continuation of and claims priority to U.S. patent application Ser. No. 17/341,949, filed Jun. 8, 2021, which is a continuation-in-part of and claims priority to U.S. patent application Ser. No. 16/366,247 filed on Mar. 27, 2019, entitled "MONITORING, PREDICTING AND ALERTING FOR CENSUS PERIODS IN MEDICAL INPATIENT UNITS." The entirety of the aforementioned applications are incorporated by reference herein.

TECHNICAL FIELD

This disclosure relates generally to adaptive learning systems (e.g., via employment of machine learning).

BACKGROUND

Data related to a hospital generally resides in different digital systems, is generated at various frequencies with respect to time, and/or employs a variety of different technologies. For instance, a vast amount of data is generally generated daily by various network-connected medical devices and/or network-connected medical systems (e.g., medical devices, medical equipment, sensors, mobile devices, controllers, medical logs, etc.) in a hospital environment. In certain instances, such data can be saved on cloud-based data infrastructure and can be stored as unstructured data. Consequently, processing, searching and/or analyzing the voluminous amounts of unstructured data associated with a hospital environment is computationally expensive. Furthermore, gleaning insights from data stored on a cloud-based data infrastructure associated with a hospital environment is generally time consuming and/or not easy to achieve.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

According to an embodiment, a system includes a grouping component, a group stability component, a model selection component and a patient census component. The grouping component defines a group of beds at a medical facility based on at least one grouping factor. For example, the grouping of beds can be based on association with a same inpatient unit or group of inpatient units. The grouping of beds can also be based on the beds being associated with the same attribute (e.g., service line, acuity level, bed type, etc.). With this example, the beds in the group may be included in same or different inpatient units. The group stability component determines a measure of occupancy variability for the group based on historical census data for respective beds in the group. The model selection component selects one or more census forecasting models for the group based on the measure of occupancy variability, wherein the number and type of the one or more census forecasting models selected by the selection component varies as a function of the measure of occupancy variability. For example, in implementations in which the measure of variability is high (indicating high variability), the model selection component may select a greater number of models relative to implementations in which the measure of variability is low.

The patient census component applies the one or more census forecasting models to current patient flow data for the medical facility to forecast an expected occupancy level for the group during one or more future periods of time. In embodiments in which the model selection component selects two or more forecasting models, the system may further comprise a forecasting optimization component that estimates weights for the different forecasting models and combines outputs of the different forecasting models using the weights to forecast the expected occupancy level.

According to another embodiment, a method is provided. The method comprises defining, by a system comprising a processor, a group of beds at a medical facility based on at least one grouping factor. The method also comprises determining, by the system, a measure of occupancy variability for the group based on historical census data for respective beds in the group. Furthermore, the method comprises selecting, by the system, one or more census forecasting models for the group based on the measure of occupancy variability. The method also comprises applying, by the system, the one or more census forecasting models to current patient flow data for the medical facility to forecast an expected occupancy level for the group during one or more future periods of time.

According to yet another embodiment, a computer readable storage device is provided. The computer readable storage device comprises instructions that, in response to execution, cause a system comprising a processor to perform operations, comprising: defining a group of beds at a medical facility based on at least one grouping factor; determining a measure of occupancy variability for the group based on historical census data for respective beds in the group; selecting one or more census forecasting models for the group based on the measure of occupancy variability, wherein the number and type of the one or more census forecasting models selected varies as a function of the measure of occupancy variability; and applying the one or more census forecasting models to current patient flow data for the medical facility to forecast an expected occupancy level for the group during one or more future periods of time.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
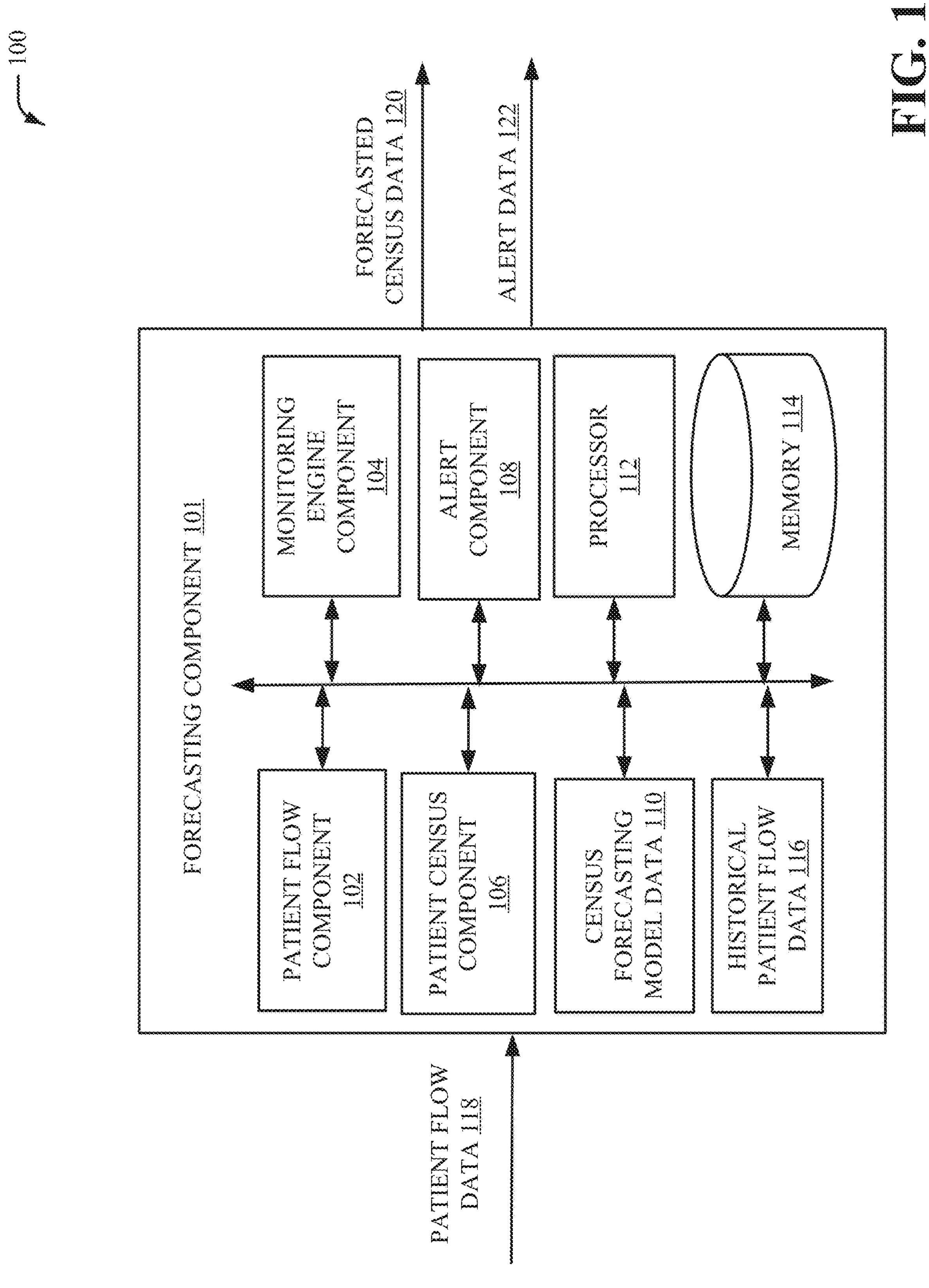
FIG. 1 illustrates a high-level block diagram of an example forecasting component, in accordance with one or more embodiments described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques for monitoring, predicting and/or alerting for census periods in medical inpatient units are presented. For instance, an adaptive learning system that monitors, predicts and/or alerts for census periods associated with medical inpatient units that satisfy a defined criterion can be provided. A medical inpatient unit can be, for example, a hospital inpatient unit. In an aspect, emerging census patterns and/or relationships (e.g., complex relationships) associated with medical inpatient units can be predicted. Furthermore, in an embodiment, real-time patient data can be collected from an electronic medical record. The real-time data can be summarized and/or aggregated to provide patient flow information. Additionally, or alternatively, historical data can be summarized and/or aggregated to provide patient flow information. Patient flow patterns and/or relationships can be learned via one or more machine learning techniques. In an aspect, percentage of patient inflows and/or patient outflows to and/or from a particular medical inpatient unit can be learning by mining historical patient movements through one or more medical inpatient units (e.g., one or more medical inpatient units that include the particular medical inpatient unit and/or one or more other medical inpatient units). Additionally, or alternatively, one or more rules of patient flow can be extracted. The one or more rules can include, for example, a rule such as automatically identify source units, volume and/or medical specialty of patients flowing to a given inpatient unit. In another embodiment, the patient flow in source units can be monitored to detect one or more abnormalities associated with the patient flow. Furthermore, census in inpatient units can be predicted and/or emerging patterns of census in source units can be detected. In yet another embodiment, an alert can be generated to alert a user of one or more census periods that satisfy a defined criterion associated with a defined threshold level.

Systems and techniques for monitoring, predicting and/or alerting for census periods associated with a grouping of beds at a medical facility are further presented. For example, hospitals often group inpatient units logically known as cohorts within a hospital or a hospital network for variety of reasons (physician assignments, staffing assignments etc.). Hence, it's important to provide accurate census forecasting at the individual unit level or cohort level. The disclosed subject matter provides a multilevel modeling approach to estimate and optimize census at multiple levels without losing accuracy because of aggregation.

In certain embodiments, an application programming interface gateway and/or a microservices architecture can be employed to collect and summarize real-time patient data throughout the patient's journey received from various sources. For example, the real-time patient data can include medical records for the patient, information regarding workflows performed for the patient, information regarding the patient's physiological status/condition (e.g., admission condition, vitals data), information regarding the patient's current location (e.g., bed/inpatient unit), information regarding encounters and events throughout the patient's journey, lab data, imaging data, and so on. The real-time patient data can, for example, be summarized per workflow process and/or strategy logic for a hospital. Data summarization of the real-time patient data can be carried out in multiple stages. In an example, a first stage can summarize data for individual patients. Furthermore, a second stage can aggregate the real-time patient data at an individual unit level, an individual bed level, a bed cohort level, and/or at a logical entity level. For example, a first stage can summarize when a patient was admitted to a medical inpatient unit and the second stage can summarize the census and total admissions within the hour for the medical inpatient unit.

In certain embodiments, an automated learning engine can deduce patient flow patterns and/or can learn patient flow relationships (e.g., complex patient flow relationships) between medical inpatient units and how the patient flow relationships impact patient census at the individual unit and bed cohort level. The automated learning engine can also deduce, for example, hourly census periods or daily census periods associated with one or more medical inpatient units and/or bed cohorts. Using the learning, the automated learning engine can, for example, predict the census for a certain interval of time (e.g., a next 1 hour to 48 hours) and can achieve very high prediction accuracy for one or more inpatient hospital units. The automated learning engine can also employ one or more supervised machine learning methodologies to determine one or more census predictions for one or more inpatient hospital units and/or bed cohorts. In certain embodiments, an alerting engine can generate one or more alerts for periods of census based on configured thresholds. For example, the one or more alerts can be generated once a census prediction is made for an inpatient hospital unit or bed cohort. In certain embodiments, a user interface service can display one or more emerging census patterns, one or more alert notifications, and/or other relevant information on a display device such as, for example, a mobile application for a mobile device, a wall display, a monitor and/or another type of display device.

Compared to a conventional system, the adaptive learning system disclosed herein can provide improved accuracy, reduced time and/or greater adaptability for monitoring, predicting, analyzing and/or alerting associated with real-time patient data for a hospital environment. The adaptive learning system disclosed herein can can also be employed to perform a utility-based analysis associated with real-time patient data for a hospital environment. As such, management of patient data for a hospital environment can be improved. Moreover, performance of systems that monitor real-time patient data for a hospital environment, predict one or more characteristics for real-time patient data for a hospital environment, analyze real-time patient data for a hospital environment, and/or generate an alert associated with real-time patient data for a hospital environment can be improved. Costs associated with the systems can also be reduced.

Referring initially to FIG. 1, there is illustrated an example system 100 that monitors, predicts and/or alerts for census periods associated with medical inpatient units that satisfy a defined criterion, according to an aspect of the subject disclosure. The system 100 can be implemented on or in connection with a network of servers associated with an enterprise application (e.g., an enterprise network of connected machines). The system 100 can be employed by various systems, such as, but not limited to healthcare systems, medical systems, hospital systems, medical device systems, electronic health record systems, electronic medical record systems, forecasting systems, adaptive learning systems, automated learning engine systems, alerting engine systems, machine learning systems, artificial intelligence systems, neural network systems, industrial systems, aviation systems, manufacturing systems, factory systems, energy management systems, power grid systems, water supply systems, transportation systems, refinery systems, media systems, research systems, financial systems, data-driven prognostics systems, network systems, computer network systems, communication systems, router systems, server systems, high availability server systems (e.g., Telecom server systems), Web server systems, file server systems, data server systems, disk array systems, powered insertion board systems, cloud-based systems, and the like. In one example, the system 100 can be associated with a Platform-as-a-Service (PaaS) and/or a medical data management system. Moreover, the system 100 and/or the components of the system 100 can be employed to use hardware and/or software to solve problems that are highly technical in nature (e.g., related to machine learning, related to digital data analysis, related to digital data analytics, etc.), that are not abstract and that cannot be performed as a set of mental acts by a human.

The system 100 can include a forecasting component 101. In FIG. 1, the forecasting component 101 includes a patient flow component 102, a monitoring engine component 104, a patient census component 106, an alert component 108, census forecasting model data 110 and historical patient flow data 118. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the forecasting component 101) can include memory 114 for storing computer executable components and instructions. The system 100 (e.g., the forecasting component 101) can further include a processor 112 to facilitate operation of the instructions (e.g., computer executable components and instructions) by the system 100 (e.g., the forecasting component 101).

The forecasting component 101 (e.g., the patient flow component 102) can receive patient flow data 118 that provides information regarding flow of patients through an inpatient medical facility (e.g., from admittance to discharge) in real-time. For example, the inpatient medical facility can include a hospital or the like that includes a plurality of different inpatient units and/or departments. The medical inpatient units can be, for example, hospital units configured to provide one or more medical services to a group of patients. The respective inpatient units can include one or more beds (e.g., hospital beds, stationary beds, mobile beds, etc.) for placing patients in association with reception of medical treatment/care at the medical facility. Each of the medical inpatient units can be associated with a location (e.g., a physical location) within a hospital or a group of hospitals. The patient flow data 118 can include medical data, sensor data, process data (e.g., process log data), monitoring data, maintenance data, parameter data, measurement data, performance data, textual data, audio data, image data, video data, machine data, asset data, equipment data, medical device data, meter data, real-time data, historical data and/or other data. Furthermore, the patient flow data 118 can be encoded data, processed data and/or raw data.

As described herein, a real-time computer system can be defined a computer system that performs its functions and responds to external, asynchronous events within a defined, predictable (or deterministic) amount of time. A real-time computer system such as system 100 typically controls a process (e.g., monitoring and forecasting patient census levels and responding to forecasted census conditions accordingly) by recognizing and responding to discrete events within predictable time intervals, and by processing and storing large amounts of data acquired from the controlled system (e.g., the patient flow data 118). Response time and data throughput requirements can depend on the specific real-time application, data acquisition and critical nature of the type of decision support provided. In the regard, the term "real-time" as used herein with reference to processing and generating information by the forecasting component 101 refers to performance of these actions within a defined or predictable amount of time (e.g., a few seconds, less than 10 seconds, less than a minute, etc.) between reception of the patient flow data 118 by the forecasting component 101. Likewise, the term real-time as used with reference to reception of the patient flow data 118 refers to reception of the patient flow data 118 by the forecasting component 101 from the one or more healthcare systems/sources within a defined or predictable amount of time (e.g., a few seconds, less than 10 seconds, less than a minute, etc.) after the corresponding information is generated by and/or received by the one or more healthcare systems/sources.

The patient flow data 118 can include a variety of rich information received from various disparate data systems/source associated with the medical facility in real-time that can be used to track occupancy levels of individual inpatient units and/or beds at the healthcare facility as a function of time, and further forecast expected occupancy levels based on learned patterns and correlations in clinical and operational attributes in the patient flow data 118 over time that influence patient flow dynamics at the medical facility. In this regard, the patient flow data 118 can not only provide information regarding number of different patients moving in and out of beds in respective inpatient units over time, but clinical and operational attributes that are relevant to understanding the dynamics of flow of patients in a hospital with varying conditions and pathways. The patient flow data 118 can thus include a variety of information regarding the patients and operating conditions of the medical facility that vary over a course of operation of the dynamic medical facility (e.g., from minute to minute, hour to hour, day to day, etc.). For example, the patient flow data 118 can include information regarding current and pending patient cases of the medical facility system, including case status information with tracking of progression of workflow events, current patient status, and the like. The patient flow data 118 can also include information current operating conditions of the medical facility system, such as current bed status and availability, current patient and staff locations, current staff assignments and tasks being performed, and the like.

In this regard, the patient flow data 118 can include patient case data that provides information regarding current and pending patient cases of the medical facility system. The terms "patient case" and "case" as used herein refers to a specific patient and a specific course or type of medical care or treatment prescribed for the patient. For example, with respect to a perioperative system, a patient case can refer to a patient and the surgical procedure or procedures prescribed for the patient. Unless otherwise stated, all patient cases involve performance of workflow, which can vary based on the type of case, the patient, and other factors.

In various embodiments, a patient case is referred to as an "active" patient case" if the defined workflow for the patient case has been initiated as defined by occurrence of a defined initial event in the workflow. A patient case can be classified as "pending" if the defined workflow for the patient case patient has not been initiated, as defined by non-occurrence of a defined initial event in the workflow that marks the start of the workflow. For example, pending patient cases can include scheduled patient cases and/or emergent patient cases (e.g., newly added/received patient cases) that have not been initiated.

In various embodiments, for all patient cases (active and pending) of the medical facility, the patient flow data 118 can include information that identifies or indicates the patient, the case (e.g., via a case number or another identifies), and the type of the case and/or procedure or procedures involved. The patient case data can also include clinical information for the patient cases regarding the patient's condition, including their reason/location of admittance, their current condition and the like. In some implementations, the patient flow data 118 can also identify and/or describe the workflow to be followed for the case, a priority level of the case, the physician/clinician(s) assigned to the case, and any defined scheduling information for the case (e.g., regarding a scheduled time/date of the case). In some implementations, forecasting component 101 can collect, extract or otherwise receive this type of patient case data from one or more case scheduling systems, clinical ordering systems, physician notes, case manager notes, and the like.

In addition, for active patient cases, the patient flow data 118 can include real-time status information regarding the progress of the case, including what's currently happening to the patient, where the patient is located, who is currently treating/attending to the patient, and the like. For example, for active patient cases, the patient flow data can include a variety of real-time status information, including but not limited to: information regarding their current workflow status in their course of treatment (e.g., in surgery, in recovery, etc.), workflow events currently being performed (e.g., procedures being performed, medications being administered, movement of the patient from location A to location B, etc.), timing of workflow events (e.g., timing of initiation and/or completion of the workflow events and procedures), staff currently involved in the patient's care (e.g., physicians, nurses, technicians, etc.), information regarding the patient's current physiological and/or medical status (e.g., stable, under anesthesia, awake, etc.) and the like. The patient flow data 118 also include real-time information regarding changes in a patient's status, condition, diagnosis, workflow (e.g., new procedures/tasks to be performed), adverse reactions, and the like. The patient flow data 118 can also reported imaging studies and corresponding radiologist reports, laboratory results, clinician notes, and other types of clinical information received for the patient over their course of care that reflects their clinical condition/status.

In this regard, patient flow data 118 can track each (or in some implementations one or more) patient's journey at the medical facility in real-time providing information regarding movement of the patient from one location to another (e.g., inpatient unit and/or bed), patient encounters and events that occur throughout the patient's journey and relevant clinical data for the patient over the patient's journey (e.g., from admittance to discharge). For example, the patient flow data 118 can include heterogenous patient data collected from various sources such as electronic medical records, workflows, lab orders/results, vitals data, locations, encounters, events, and so one.

It should be appreciated that the level of granularity of tracked workflow events, patient encounters, patient conditions, operating conditions, etc., and the specific workflow events, patient encounters, patient conditions, operating conditions, etc., that are tracked can vary. The tracked case status information can not only indicate a current status of a patient's case relative to a defined workflow, but further track the timing of workflow events, including timing of initiation, completion and/or duration of the respective workflow events. For example, the tracked case status information can indicate that a patient is currently in intensive care unit and has been there for N minutes. In this regard, the tracked case status information can include timestamps that reflect when certain workflow events are initiated and/or completed and/or indicate the duration of time a workflow event has been in progress. The tracked case status information can also include many other trackable parameters related to a patient's course of care, including information regarding patient location, patient physiological status, staff involved in the patient's care, medical equipment/supplies involved in the patient's care, and the like.

The forecasting component 101 can regularly and/or continuously receive the various types of patient flow data 118 discussed above from a variety of data systems/sources of the medical facility in real-time. For example, the forecasting component 101 can receive patient flow data 118 from one or more from case status tracking systems, patient location tracking systems/devices, patient vital signs monitoring systems, medical monitoring devices associated with the patients, and the like. In some implementations, these tracking and/or monitoring systems/devices can include systems/devices configured to receive and report user input in real-time explicitly identifying and/or indicating such status information (e.g., regarding the patient's active case status, location, workflow event progress, staff involved, etc.). These tracking and/or monitoring systems/devices can also include intelligent systems/devices configured to determine and report various real-time status information without or with minimal manual input based on analysis of sensor/device captured data signals. For example, these tracking and/or monitoring systems/devices can also include systems/devices configured determine information regarding what's currently happening to the patient (e.g., workflow events), where the patient is currently located, who is currently treating/attending to the patient, and the like based on analysis of a variety of captured data, including but not limited to: image data (e.g., using object recognition and/or other image pattern recognition technologies), audio data (e.g., using speech to text and natural language processing NPL), motion sensor data (e.g., using motion pattern recognition technology), radio frequency (RF) data, temperature sensor data, light sensor data, infrared (IR) senor data, biometric sensor data, and the like.

The patient flow data 118 can also include operating conditions data regarding the current operating conditions and/or context of the medical facility in association with flow of patients throughout the medical facility. For instance, the operating conditions data can include status information associated with one or more medical procedures performed within the medical inpatient units, time information associated with one or more medical procedures performed within the medical inpatient units, statistical information associated with one or more medical procedures performed within the medical inpatient units, efficiency information associated with one or more medical procedures performed within the set medical inpatient units, and/or other information associated with one or more medical procedures performed within the medical inpatient units. The operations data can additionally or alternatively include information associated with medical staff within the medical inpatient units. For example, the operations data can include status information associated with medical staff within the medical inpatient units, time information associated with medical staff within the medical inpatient units, location information associated with medical staff within the medical inpatient units, statistical information associated with medical staff within the medical inpatient units, efficiency information associated with medical staff within the medical inpatient units, and/or other information associated with medical staff within the medical inpatient units.

For example, in implementations in which the medical facility system is a hospital, a perioperative system or a similar type of system, the operating conditions data can include information regarding but not limited to: current occupancy levels, current bed availably, current bed status (e.g., occupied, clean or dirty), number of patient waiting for beds, staff availability, staff location, staff activity, supply/instrument availability and location, equipment status and location (e.g., and the like. In this regard, with respect medical facility wherein patients move to different procedural areas and beds over the course of their inpatient workflow/journey, the patient flow data 118 can include current bed status information identifying the availability status of beds in the different procedural areas, including where they are located, type of bed (e.g., in systems which have different types of beds for different types of medical needs), and whether the bed is occupied, available, dirty, and the like. In some implementation in which a bed is occupied, dirty or otherwise unavailable, the patient flow data 118 can also indicate an expected time when the bed will become available. Similarly, the patient flow data 118 can indicate the current status of procedure areas (e.g., operating rooms), including whether there are available, in-use, being cleaned/sterilized, etc. The current operation conditions data can also include information regarding the current status of equipment (e.g., in use or available, being cleaned, dirty, etc.).

The patient flow data 118 can include resource data associated with the medical facility. The resource data can be associated with one or more resources associated with the medical inpatient units. For example, the resource data can include medication information utilized within the medical inpatient units, medical supplies information utilized within the medical inpatient units, medical equipment information utilized within the medical inpatient units, and/or other resource information utilized within the medical inpatient units. In another embodiment, the patient flow data 118 can provide aggregated information associated with the patient data, the operations data and/or the resource data.

The patient flow data 118 can also include information regarding staff, including the identities of staff currently working and/or available, where they are currently located, what they are currently doing, where they are currently assigned, and the like. For example, the current staff information can identify the staff (e.g., nurses, physicians, technicians, etc.) currently assigned to specific procedure areas and/or bed, cases, patients and the like, and their scheduled work hours/time frame (e.g., nurse Amy N. is assigned to postoperative room number 152 until 6:00 pm). The current staff information can also identify tasks and/or activities currently being performed by and/or assigned for performance by specific staff members. In this regard, the activity information can identify or indicate whether a staff member is available, busy, with a patient, when they will be available to perform another task and the like. In another example, with respect to surgeons in particular, the staff data can indicate a current status/activity of a surgeon, including whether they are sterilized and ready (and waiting) to perform surgery, whether they are currently in surgery, whether the surgeon is currently preparing (e.g., being re-sterilized), etc.

The patient flow data 118 an also include various other type of contextual data associated with the medical facility that can or has been shown to historically effect and/or correlate to (e.g., either directly or indirectly) the operations of the medical facility system with respect to case workflow timing, supply/demand for resources, patient occupancy levels, bed availability levels, reception of emergent patients, patient cancelations and delays, patient complications, and the like. For example, in some implementations, the patient flow data 118 can include information regarding time of day, day of week/year, localized events or conditions at the medical facility (e.g., emergency or crisis scenarios, disease outbreaks), local events associated high influx of patients, etc.) and the like.

In an aspect, the patient flow data 118 can be generated by one or more devices and/or one or more equipment located within the set of medical inpatient units. For example, the patient data can be generated by one or more medical devices, one or more medical equipment, one or more sensors, one or more mobile devices, one or more computers, one or more tablet computers, and/or one or more other devices. In certain embodiments, the patient data can be generated by one or more surgical instruments such as, but not limited to, one or more anesthetic machines, one or more post anesthetic care machines, surgical tracking software, and/or another type of surgical instrument. Furthermore, the one or more devices and/or one or more equipment located within the set of medical inpatient units can be one or more network-connected devices and/or one or more network-connected equipment. In another aspect, the patient data can be obtained from one or more medical logs. For example, the patient data can be obtained from one or more electronic medical records.

In various embodiments, as real-time patient flow data 118 is received, the real-time patient flow data can be stored as historical patient 116 over time. For example, the historical patient flow data 116 can include patient flow data 118 aggregated for the medical facility over time. In this regard, the forecasting component 101 can collect and log sets of the patient flow data 118 over time (e.g., once an hour, once a day, etc.) to generate historical patient flow data 118 that can be used for developing and/or training/updating various one census forecasting machine learning models.

The patient flow component 102 can perform a first machine learning process to learn one or more patterns in the historical patient flow data 116 and/or the patient flow data 118 as it is received in real-time. The patient flow component 102 can perform the first machine learning process to additionally or alternatively learn one or more relationship (e.g., one or more complex relationships) associated with the historical patient flow data 116 and/or the patient flow data 118 as it is received in real-time. Additionally, or alternatively, the first machine learning process performed by the patient flow component 102 can determine one or more rules associated with the historical patient flow data 116. Additionally, or alternatively, the first machine learning process performed by the patient flow component 102 can determine one or more relationships among the set of medical inpatient units. The patient flow component 102 can employ principles of artificial intelligence to facilitate learning one or more patterns in the historical patient flow data 116 and/or the patient flow data 118 as it is received in real-time, determining one or more rules associated with the historical patient flow data 116, and/or determining one or more relationships among the set of medical inpatient units. The patient flow component 102 can perform learning associated with the historical patient flow data 116, and/or the patient flow data 118 as it is received in real-time, explicitly or implicitly. Learning and/or determining inferences by the patient flow component 102 can facilitate identification and/or classification of different patterns associated with the historical patient flow data 116 and/or the patient flow data 118 as it is received in real-time, determining one or more rules associated with the historical patient flow data 116, and/or determining one or more relationships among the set of medical inpatient units. The patient flow component 102 can also employ an automatic classification system and/or an automatic classification process to facilitate learning one or more patterns in the historical patient flow data 116 and/or the patient flow data 118 as it is received in real-time, determining one or more rules associated with the historical patient flow data 116, and/or determining one or more relationships among the set of medical inpatient units. For example, the patient flow component 102 can employ a probabilistic and/or statistical-based analysis (e.g., factoring into the analysis utilities and costs) to learn one or more patterns in the historical patient flow data 116, determine one or more rules associated with the historical patient flow data 116, and/or determine one or more relationships among the set of medical inpatient units. The patient flow component 102 can employ, for example, a support vector machine (SVM) classifier to learn one or more patterns in the historical patient flow data 116 and/or the patient flow data 118 as it is received in real-time, determine one or more rules associated with the historical patient flow data 116, and/or determine one or more relationships among the set of medical inpatient units. Additionally, or alternatively, the patient flow component 102 can employ other classification techniques associated with Bayesian networks, decision trees and/or probabilistic classification models. Classifiers employed by the patient flow component 102 can be explicitly trained (e.g., via a generic training data) as well as implicitly trained (e.g., via observing user behavior, receiving extrinsic information). For example, with respect to SVM's that are well understood, SVM's are configured via a learning or training phase within a classifier constructor and feature selection module. A classifier is a function that maps an input attribute vector, x=(x1, x2, x3, x4, xn), to a confidence that the input belongs to a class—that is, f (x)=confidence (class).

In an aspect, the patient flow component 102 can include an inference component that can further enhance automated aspects of the patient flow component 102 utilizing in part inference-based schemes to facilitate learning one or more patterns in the historical patient flow data 116 and/or the patient flow data 118 as it is received in real-time, determining one or more rules associated with the historical patient flow data 116, and/or determining one or more relationships among the set of medical inpatient units. The patient flow component 102 can employ any suitable machine-learning based techniques, statistical-based techniques and/or probabilistic-based techniques. The patient flow component 102 can additionally or alternatively employ a reduced set of factors (e.g., an optimized set of factors) to facilitate providing a most accurate machine learning model for predicting census in respective medical inpatient units. For example, the patient flow component 102 can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the patient flow component 102 can perform a set of machine learning computations associated with the historical patient flow data 116 and/or the patient flow data 118 as it is received in real-time. For example, the patient flow component 102 can perform a set of clustering machine learning computations, a set of decision tree machine learning computations, a set of instance-based machine learning computations, a set of regression machine learning computations, a set of regularization machine learning computations, a set of rule learning machine learning computations, a set of Bayesian machine learning computations, a set of deep Boltzmann machine computations, a set of deep belief network computations, a set of convolution neural network computations, a set of stacked auto-encoder computations and/or a set of different machine learning computations. The one or more patterns, the one or more rules and/or the one or more relationships determined by the patient flow component 102 can be stored, for example, in a machine learning database and/or the memory 114.

In certain embodiments, the one or more patterns in the historical patient flow data 116 and/or the patient flow data 118 as it is received in real-time (e.g., the one or more patterns learned by the first machine learning process) can be configured as one or more digital fingerprints (e.g., one or more digital signatures) that represents one or more digital patterns associated with the historical patient flow data 116 and/or the patient flow data 118. A digital fingerprint can be a string of bits associated with a portion of the historical patient flow data 116 and/or the patient flow data 118. A digital fingerprint can also include a set of data values for one or more parameters over a defined period of time associated with the historical patient flow data 116 and/or the patient flow data 118. In certain implementations, a digital fingerprint can comprise a sequence of sub-fingerprints associated with different patterns in the historical patient flow data 116 and/or the patient flow data 118. Furthermore, a digital fingerprint can uniquely identify and/or convey a pattern in the historical patient flow data 116 and/or the patient flow data 118. For example, a digital fingerprint can be a data element that encodes a pattern in the historical patient flow data 116 and/or the patient flow data 118. A digital fingerprint can also be associated with a timestamp and/or a period of time for the historical patient flow data 116 and/or the patient flow data 118. The patient flow component 102 can employ one or more digital fingerprinting techniques (e.g., one or more digital fingerprint algorithms) to map at least a portion of the historical patient flow data 116 and/or the patient flow data 118 into a set of digital fingerprints. For example, the patient flow component 102 can employ a hash technique to generate the set of digital fingerprints associated with the one or more patterns in the historical patient flow data 116 and/or the patient flow data 118. In another example, the patient flow component 102 can employ a locality sensitive hashing technique to generate the set of digital fingerprints associated with the one or more patterns in the historical patient flow data 116 and/or the patient flow data 118. In yet example, the patient flow component 102 can employ a random hashing technique to generate the set of digital fingerprints associated with the one or more patterns in the historical patient flow data 116 and/or the patient flow data 118. In an implementation, a digital fingerprint can comprise min-hash values associated with a portion of the historical patient flow data 116 and/or the patient flow data 118. For example, a digital fingerprint can comprise a vector of min-hash values associated with a portion of the historical patient flow data 116 and/or the patient flow data 118. In another example, a digital fingerprint can comprise a band of min-hash values associated with a portion of the historical patient flow data 116 and/or the patient flow data 118. In yet another example, a digital fingerprint can comprise a locality-sensitive hashing band of min-hash values associated with a portion of the historical patient flow data 116 and/or the patient flow data 118. However, it is to be appreciated that other types of digital fingerprinting techniques and/or hashing techniques can be employed to generate a digital fingerprint associated with the historical patient flow data 116 and/or the patient flow data 118.

The monitoring engine component 104 can monitor the one or more patterns in the patient flow data 118 as new patient flow data come in. Additionally, or alternatively, the monitoring engine component 104 can monitor the one or more rules associated with the patient flow data 118 as new patient flow data comes in. Additionally, or alternatively, the monitoring engine component 104 can monitor the one or more relationships among the set of medical inpatient units. In an aspect, the monitoring engine component 104 can perform a second machine learning process to detect one or more abnormalities associated with the one or more patterns in the patient flow data 118. For instance, the one or more abnormalities associated with the one or more patterns in the patient flow data 118 can be unique behavior and/or unique characteristics associated with the one or more patterns in the patient flow data 118. In an example, an abnormality associated with the one or more patterns in the patient flow data 118 can be a change or a difference with respect to one or more other predetermined patterns in the historical patient flow data 116. In certain embodiments, the monitoring engine component 104 can compare the one or more patterns in the patient flow data 118 to one or more other patterns (e.g., one or more predetermined patterns) to facilitate detection of the one or more abnormalities. In an embodiment, the one or more abnormalities associated with the one or more patterns in the patient flow data 118 can predict and/or indicate an event associated with the one or more patterns in the patient flow data 118. A match between a pattern and another pattern can be, for example, approximately an exact match. Alternatively, a match between a pattern and another pattern can be, for example, a fuzzy match. The monitoring engine component 104 can, in certain embodiments, compute similarity between a pattern and another pattern based on one or more pattern recognition techniques, one or more statistical techniques, and/or one or more artificial intelligence techniques. In another embodiment, the monitoring engine component 104 can additionally or alternatively compute similarity between a pattern and another pattern based on a distance metric. For example, the monitoring engine component 104 can compute similarity between a pattern and another pattern based on a Hamming distance. In another example, the monitoring engine component 104 can compute similarity between a pattern and another pattern based on based on a Jaccard distance. However, one or more other mechanisms for computing similarity between a pattern and another pattern can additionally or alternatively be employed.

The monitoring engine component 104 can employ principles of artificial intelligence to facilitate monitoring the one or more patterns in the patient flow data 118 and/or generating the one or more abnormalities associated with the one or more patterns in the patient flow data 118. In certain embodiments, the monitoring engine component 104 can include a prediction component that employs data (e.g., real-time data and/or historical data) to monitor a current state of the set of medical inpatient units. Additionally, the monitoring engine component 104 can facilitate prediction of emerging census patterns for the set of medical inpatient units. The monitoring engine component 104 can perform monitoring of one or more patterns in the patient flow data 118 explicitly or implicitly. Learning and/or determining inferences by the monitoring engine component 104 can facilitate monitoring of one or more patterns in the patient flow data 118. The monitoring engine component 104 can also employ an automatic classification system and/or an automatic classification process to facilitate monitoring one or more patterns in the patient flow data 118. For example, the monitoring engine component 104 can employ a probabilistic and/or statistical-based analysis (e.g., factoring into the analysis utilities and costs) to monitor one or more patterns in the patient flow data 118. The monitoring engine component 104 can employ, for example, an SVM classifier to monitor one or more patterns in the patient flow data 118. Additionally, or alternatively, the monitoring engine component 104 can employ other classification techniques associated with Bayesian networks, decision trees and/or probabilistic classification models. Classifiers employed by the monitoring engine component 104 can be explicitly trained (e.g., via a generic training data) as well as implicitly trained (e.g., via observing user behavior, receiving extrinsic information). For example, with respect to SVM's that are well understood, SVM's are configured via a learning or training phase within a classifier constructor and feature selection module. A classifier is a function that maps an input attribute vector, x=(x1, x2, x3, x4, xn), to a confidence that the input belongs to a class—that is, f (x)=confidence (class).

In an aspect, the monitoring engine component 104 can include an inference component that can further enhance automated aspects of the monitoring engine component 104 utilizing in part inference-based schemes to facilitate monitoring of one or more patterns in the patient flow data 118. The monitoring engine component 104 can employ any suitable machine-learning based techniques, statistical-based techniques and/or probabilistic-based techniques. The monitoring engine component 104 can additionally or alternatively employ a reduced set of factors (e.g., an optimized set of factors) to facilitate providing a most accurate machine learning model for predicting census in respective medical inpatient units. For example, the monitoring engine component 104 can employ expert systems, fuzzy logic, SVMs, HMMs, greedy search algorithms, rule-based systems, Bayesian models (e.g., Bayesian networks), neural networks, other non-linear training techniques, data fusion, utility-based analytical systems, systems employing Bayesian models, etc. In another aspect, the monitoring engine component 104 can perform a set of machine learning computations associated with the one or more patterns in the patient flow data 118. For example, the monitoring engine component 104 can perform a set of clustering machine learning computations, a set of decision tree machine learning computations, a set of instance-based machine learning computations, a set of regression machine learning computations, a set of regularization machine learning computations, a set of rule learning machine learning computations, a set of Bayesian machine learning computations, a set of deep Boltzmann machine computations, a set of deep belief network computations, a set of convolution neural network computations, a set of stacked auto-encoder computations and/or a set of different machine learning computations. The one or more abnormalities determined by the monitoring engine component 104 can be stored, for example, in a machine learning database and/or the memory 114.

The patient census component 106 can determine patient census data associated with the patient flow data 118. In some embodiments, the patient census data can include forecasted census data 120 that provides a prediction for a total number of patient identities in one or more of the medical inpatient units during a period of time. For example, the forecasted census data 120 can provide a prediction for a total number of patients that will utilize beds within the one or more medical inpatient units of the medical facility during a future period of time. The forecasted census data 120 can additionally or alternatively provide a prediction associated with medical assets in one or more medical inpatient units. For example, the forecasted census data 120 can predict a total number of beds that will be available (e.g., unoccupied) and unavailable (e.g., occupied by a patient or otherwise closed for staffing or maintenance reasons). The forecasted census data 120 can additionally or alternatively provide one or more predicted emerging patterns in the set of medical inpatient units during the period of time (e.g., the future period of time).

The patient census component 106 can determine or infer the forecasted census data 120 based on the one or more patterns and/or the one or more abnormalities. In certain embodiments, the patient census component 106 can employ data collected in real time to determine the patient census data associated with the patient flow data 118. Additionally, or alternatively, the patient census component 106 can employ historical data to determine the patient census data associated with the patient flow data 118. Additionally, or alternatively, the patient census component 106 can employ learning and/or prediction to determine the patient census data associated with the patient flow data 118. In an embodiment, the patient census component 106 can determine the patient census data for a given point in time (e.g., a census for a particular medical inpatient unit at 6:00 am, etc.). In another embodiment, the patient census component 106 can determine the patient census data over multiple time periods and/or with different time intervals between predictions.

In various embodiments, the patient census component 106 can employ one or more previously trained/developed census forecasting models to generate the forecasted census data 120. In the embodiment shown, these census forecasting models are represented by census forecasting model data 110. With these embodiments, the patient census component 106 can extract the relevant input parameters/parameter values from the patient flow data 118 for processing by the one or more census forecasting models. The patient census component 106 can further apply the census forecasting models to the extracted input data to generate the forecasted census data 120. The one or more census forecasting models can include machine learning models that have been previously configured to process the extracted parameters from the patient flow data 118 and generate the forecasted census data 120 based on learned patterns and correlations between various patient and operational attributes that influence patient flow as deduced from the historical patient flow data 116 (e.g., by the patient flow component 102).

In some embodiments, the census forecasting models can include separate models tailored for individual inpatient units. With these embodiments, the patient census component 106 can apply the model for a specific unit to generate forecasted census data 120 for that unit for future period (or point) of time. Additionally, or alternatively, the census forecasting models can include separate models tailored for various bed grouping cohorts, as discussed in greater detail with reference to FIG. 6. The census forecasting model(s) for a specific unit and/or bed cohort can also be adapted to generate census forecasts for different periods of time based on the current patient flow data for the medical facility. For example, the patient census component 106 may adjust the output variable (e.g., the Y variable) of the census forecasting models for different time periods to generate a forecasted occupancy level of the specific unit and/or bed cohort for each hour in an upcoming 48-hour time frame. Additionally, or alternatively, the census forecasting models can include separate models for different time periods. For example, the census forecasting models can include a first model that estimates the census forecast for a given inpatient unit (and/or bed cohort) for next hour, a second model that estimates the census forecast for the second hour, a third model that estimates the census forecast for the third hour, and so on. Techniques for training and developing the census forecasting models are discussed infra with reference to FIG. 8.

The alert component 108 can generate alert data 122 based on the forecasted census data 120. In an aspect, the alert data 122 generated by the alert component 108 can include one or more alerts for one or more user interfaces. The alert component 108 can generate the alert data 122 (e.g., the alert component 108 can generate the one or more alerts for the one or more user interfaces) in response to a determination that the forecasted census data 120 satisfies a defined criterion. In an embodiment, the alert component 108 can generate the alert data 122 (e.g., the alert component 108 can generate the one or more alerts for the one or more user interfaces) in response to a determination that the forecasted census data 120 exceeds a defined threshold. For example, the alert component 108 can generate the alert data 122 (e.g., the alert component 108 can generate the one or more alerts for the one or more user interfaces) in response to a determination that the forecasted census data 120 indicates an extreme census period for one or more medical inpatient units of the medical facility. The alert data 122 can include one or more different alerts that are uniquely configured, displayed and/or generated. In an embodiment, the alert component 108 can provide the alert data 122 (e.g., the alert component 108 can provide the one or more alerts) to a display device such as, for example, a mobile device, a mobile application for a mobile device, a wall display, a monitor and/or another type of display device. In certain embodiments, the alert data 122 (e.g., the one or more alerts) can alter a graphical element and/or a graphical indicator for a user interface. For example, the alert data 122 (e.g., the one or more alerts) can alter a color of a graphical element associated with a user interface. In certain embodiments, the alert component 108 can generate the user interface, for display on the display device, that outputs the alert data 122 and/or the patient census data in a human interpretable format. In certain embodiments, the alert data 122 can provide an indicator associated with one or more emerging census patterns in the set of medical inpatient units. In certain embodiments, the alert component 108 can display real time data in a user-friendly format.

While FIG. 1 depicts separate components in the forecasting component 101, it is to be appreciated that two or more components may be implemented in a common component. Further, it can be appreciated that the design of system 100 and/or the forecasting component 101 can include other component selections, component placements, etc., to facilitate census forecasting for one or more medical inpatient units.

Figure 2:
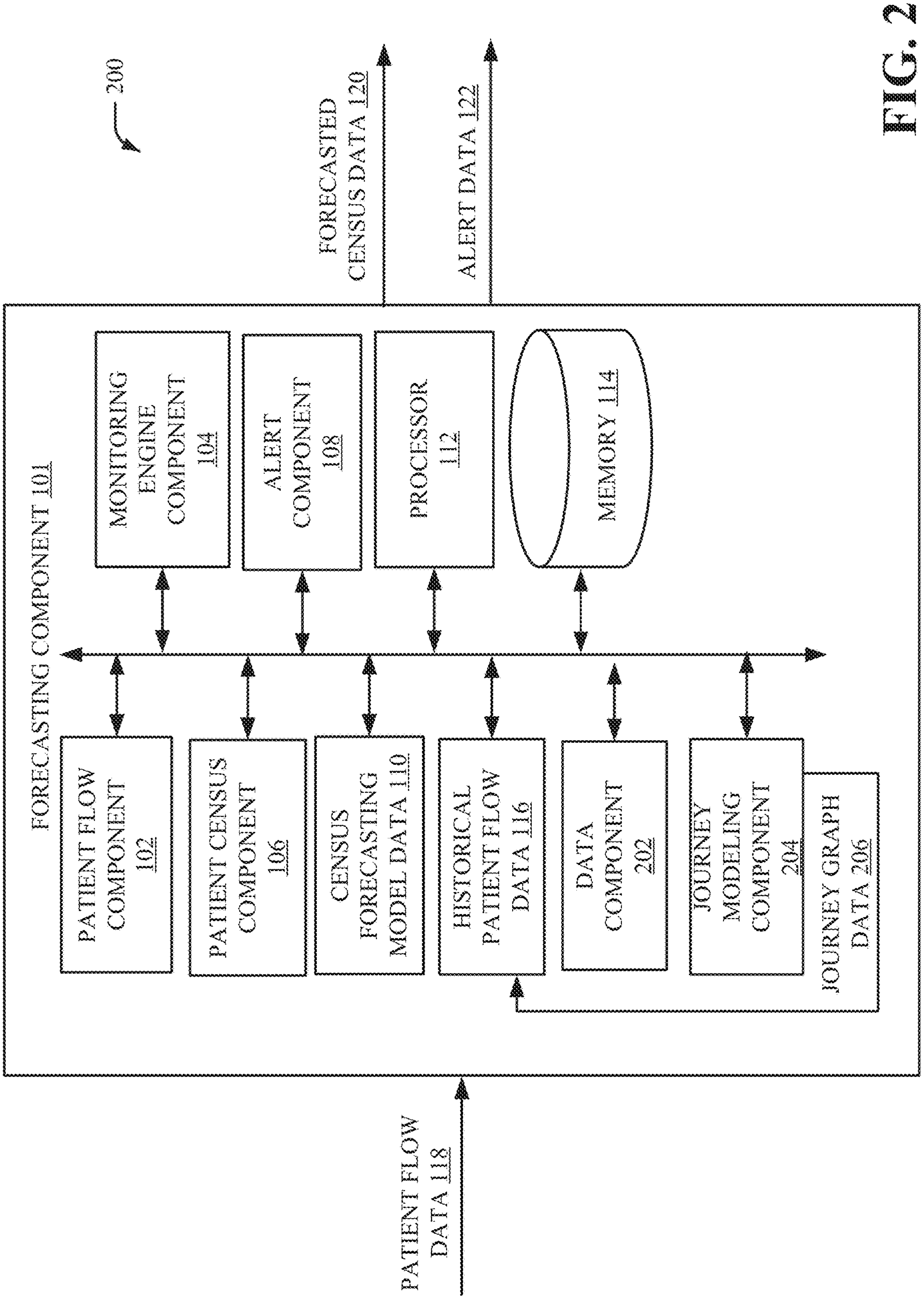
FIG. 2 illustrates a high-level block diagram of another example forecasting component, in accordance with one or more embodiments described herein.

Referring now to FIG. 2, there is illustrated a non-limiting implementation of a system 200 in accordance with various aspects and implementations of this disclosure. System 200 can include same or similar component as system 100 with the addition of data component 202 and journey modeling component 204 to the forecasting component 101. Repetitive description of like elements employed in other embodiments described herein is omitted for sake of brevity.

The data component 202 can collect at least a portion of the patient flow data 118 and generate the historical patient flow data 116. In some embodiments, the data component 202 can generate historical census information from the historical patient flow data 116 that calculates the number of patients in each inpatient unit and/or bed at the medical facility as a function of time (e.g., in hourly increments over time or in other time frame increments). The historical census data can be included in the historical patient flow data 116.

In an aspect, the data component 202 can collect at least a portion of the patient flow data 118 from multiple data sources associated with an electronic medical record system. For instance, the data component 202 can collect the patient data, the operations data and/or the resource data from multiple data sources associated with an electronic medical record system. Additionally, or alternatively, the data component 202 can collect the patient data, the operations data and/or the resource data from multiple devices and/or multiple equipment located within the set of medical inpatient units. In an embodiment the data component 202 can aggregate the patient data, the operations data and/or the resource data to generate the patient flow data 118. Additionally, or alternatively, the data component 202 can summarize the patient data, the operations data and/or the resource data based on data associated with a set of patient identities. For example, the data component 202 can group the patient data, the operations data and/or the resource data based on a corresponding patient identity (e.g., a corresponding patient). Additionally, or alternatively, the data component 202 can summarize the patient data, the operations data and/or the resource data based on data associated with the set of medical inpatient units. For example, the data component 202 can group the patient data, the operations data and/or the resource data based on a corresponding medical inpatient unit. In an embodiment, the data component 202 can transform the patient data, the operations data and/or the resource data into a data format associated with machine learning. Additionally, or alternatively, the data component 202 can transform the patient flow data 118 and/or the historical patient flow data 116 into a data format associated with machine learning.

Figure 3:
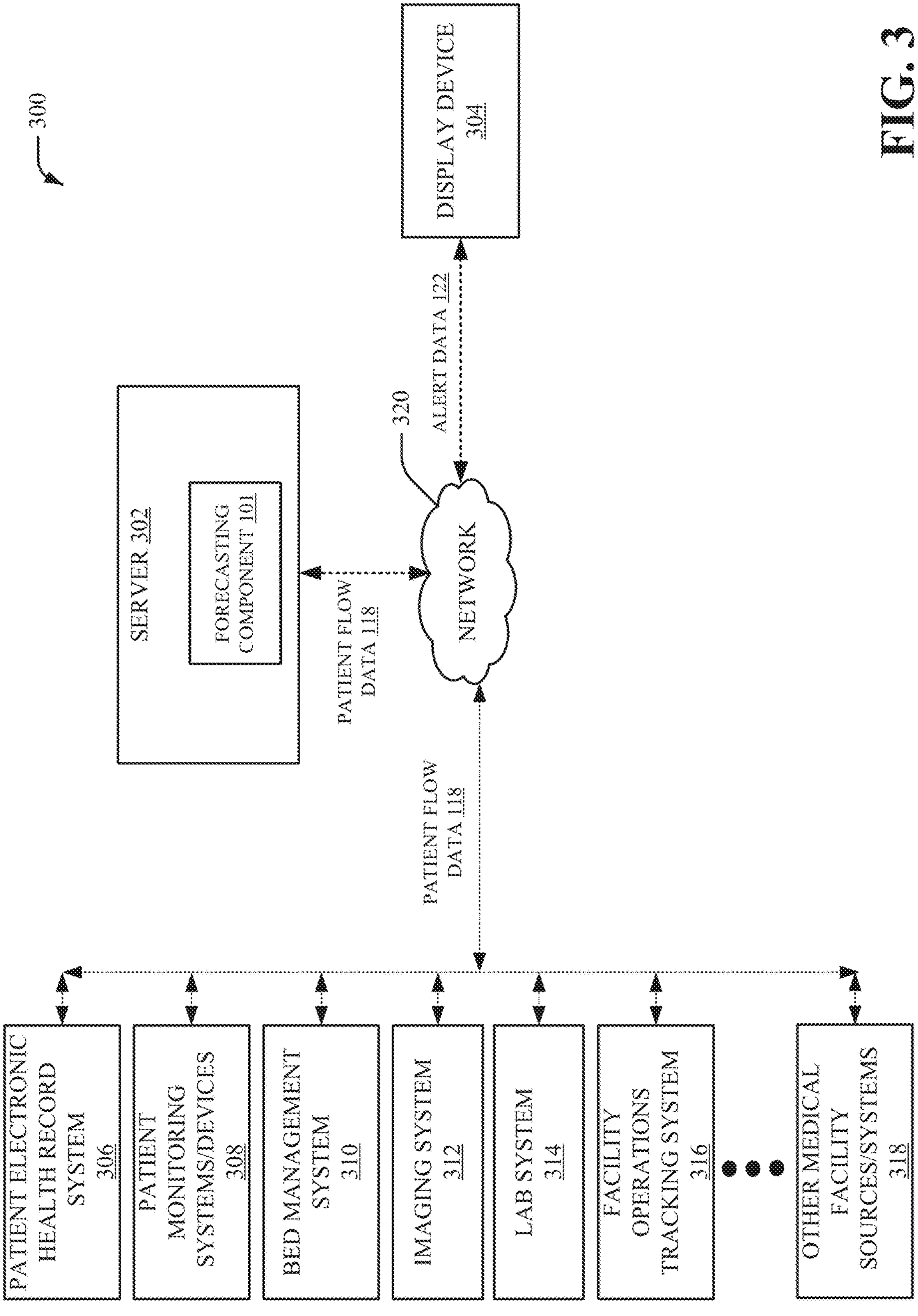
FIG. 3 illustrates an example system for monitoring, predicting and/or alerting for census periods in medical inpatient units, in accordance with one or more embodiments described herein.

FIG. 3 illustrates a non-limiting implementation of a system 300 in accordance with various aspects and implementations of this disclosure. Repetitive description of like elements employed in other embodiments described herein is omitted for sake of brevity.

The system 300 includes a server 302, a display device 304 and a plurality of different data sources and systems from which the data component 202 may collect/receive/extract the patient flow data 118. These data source/systems may include for example, a patient electronic health record (EHR) system 306, patient monitoring systems/devices 308, a bed management system 310, an imaging system 312, a laboratory system 314, a facility operations tracking system 316 and other medical facility sources/systems 318. For example, the patient EHR system 306 can provide a variety of patient information regarding their medical history, the current reported diagnosis/condition, and clinical notes/reports as well as demographic information for the respective patients that flow through the medical facility. The patient monitoring systems/devices 308 may include various devices and/or systems that track and provide real-time information regarding the current location of the patients, the events and conditions that occur throughout the patient's journey, the clinical status of the patient's, the physiological status of the patients (e.g., vitals) and so on.

The bed management system 310 can provide patient flow information 118 regarding current bed placement locations (e.g., inpatient units and/or specific beds) of patients and pending placement requests for beds. For instance, in some implementations, the bed management system 310 can include a system that aggregates and manages all bed requests for the medical facility, including bed requests of different types and/or bed requests associated with different medical units throughout the healthcare facility. In association with managing placement requests, the bed management system(s) can provide a variety of information associated with the patient placement requests. For example, the placement requests can be associated with information regarding details of the requests, such as but not limited to: the type of bed and medical service associated with the request, one or more preferred destination medical units for fulfilling the request, an order type associated with the request, priority information defined for the request, assignment urgency information associated with the request, a type of room requested, event information regarding what triggered the request, clinician instructions regarding specific care instructions for the patient, and the like. The bed management systems can also provide information identifying timing of reception of respective placement requests. current status of the respective requests (e.g., pending, fulfilled, on-hold, etc.), total number of pending requests at the healthcare facility, total number of pending requests per unit, number of pending requests clustered by request type, and the like.

The placement requests can also include information regarding the patient for which a request is made, such as but not limited to: information identifying the patient, a current state/condition of the patient, demographic information for the patient, information regarding preferences of the patient, insurance information for the patient, and the like. The bed management system 310 can also provide policy information regarding bed placement policy rules for the medical facility.

The imaging system 312 can provide medical image data and associated reports generated for the respective patients that flow through the medical facility. For example, the patient flow data 118 can include information reported by the imaging system 312 identifying timing of a medical image study conducted and the radiologist report for the study, the actual image data and so on. Similarly, the laboratory system 314 can provide medical laboratory data and associated reports generated for the respective patients that flow through the medical facility. For example, the patient flow data 118 can include information reported by the laboratory system 314 identifying lab orders, lab results and so one, reported in real-time. The facility operations tracking system 316 can generate and provide patient flow data 118 regarding various dynamic operational conditions of the medical facility.

It should be appreciated that these patient flow data 118 sources/systems are merely exemplary and other or alternative types of healthcare data sources/system are envisioned that may provide the patient flow data 118.

The server 302 can include the forecasting component 101. Furthermore, the various patient flow data 118 sources can be one or more network-connected devices communicatively coupled to the server 302. In this regard, the server 302, the patient flow data 118 source/systems, and/or the display device 304 can be in communication via a network 320. The network 320 can be a communication network, a wireless network, an internet protocol (IP) network, a voice over IP network, an internet telephony network, a mobile telecommunications network and/or another type of network. The display device 304 can be a mobile device, a mobile application for a mobile device, a wall display, a monitor, a computer, a tablet computer, a wearable device, and/or another type of display device. In an embodiment, the various patient flow data 118 source/systems can provide the patient flow data 118 to the forecasting component 101 of the server 402 via the network 320. Additionally, or alternatively, the forecasting component 101 of the server 302 can provide the alert data 122 to the display device 304 via the network 320.

In an embodiment, the system 300 can be a microservices architecture that can collect and/or aggregate the patient flow data 118 from the various patient flow data 118 source/systems associated with the medical facility into the historical patient flow data 116. Using the historical patient flow data 116, the forecasting component 101 can employ one or more machine learning techniques to learn patient flow patterns, deduce rules and establish complex relationships between various clinical and operational attributes associated with events and encounter that occur throughout the patient journey that influence why, when and where they are placed in certain units and/or beds. The forecasting component 101 can also employ one or more machine learning techniques to monitor patient flow patterns and detect abnormalities in patient flow associated with new patient flow data 118 as it is received. Furthermore, the forecasting component 101 can employ one or more machine learning techniques to predict census levels (e.g., forecasted occupancy levels) at one or more medical inpatient units and/or bed cohorts. The display device 306 can be employed to alert users (e.g., administrators, medical staff, doctors, nurses, etc.) of emerging census patterns associated with the patient flow data 118.

In another embodiment, the system 300 can be an adaptive machine learning system that employs patient data, operations data and/or resource data associated with the patient flow data 118. The forecasting component 101 can learn one or more aspects of hospital operations associated with the set inpatient units and/or bed cohorts automatically adapt to policy changes of a hospital (e.g., a new policy can state that half of the patients in a medical inpatient unit can be surgical patients because of nurse credentials), and/or detect emerging patterns of census in the medical inpatient units over a future time horizon (e.g., up to 48 hours) with improved accuracy. As such, the system 300 can employ machine learning analytics in combination with hospital knowledge to obtain an accurate, holistic view throughout an entire health system. Accordingly, better care for patients can be provided, improved access for patients can be provided, costs for a medical system can be reduced, and/or revenue opportunities for a hospital can be increased.

In yet another embodiment, the system 300 can provide one or more microservices that can be tailored and/or configured to the collect a specific type of data at a desired frequency. For example, a portion of the patient flow data 118 can be pushed and/or collected in real time while another portion of the patient flow data 118 can be batched and/or pulled periodically and stored as historical patient flow data 116. The forecasting component 101 can facilitate communication of microservices across service boundaries. The forecasting component 101 can also integrate and/or aggregate the patient flow data 118 for artificial intelligence-based analytics. The forecasting component 101 can provide a machine learning engine combined with heuristic algorithms to combine results of multiple machine learning models. Additionally, or alternatively, the forecasting component 101 can provide spectral analysis to detect patient flow patterns associated with one or more medical inpatient units. Patient flow patterns can observe a volume of patients moving between medical inpatient units by hour, time of day, day of week, medical specialty, current occupancy levels, business rules and/or one or more other factors. The machine learning engine of the forecasting component 101 can also extract one or more rules and/or can create one or more machine learning models for the patient flow patterns.

The forecasting component 101 can also monitor the patient flow patterns associated with the patient flow data 118 and can detect one or more changes to the flow patterns beyond pre-determined thresholds. The forecasting component 101 can also predict medical inpatient unit and/or bed cohort census based on flow patterns and cam provide one or more alerts to the display device 304 if the emerging patterns of census are beyond configured limits. In certain embodiments, the limits can be learned from normal operating patterns of a hospital system to assist in setting the thresholds. An alert engine of the forecasting component 101 can create and/or display one or more alerts regarding the emerging census patterns using one or more user interface services associated with the display device 304.

With reference again to FIG. 2, in one or more embodiments, the journey modeling component 204 can model patient flow data 118 for individual patients in the form of a heterogenous graph network representing their journey through the medical facility. For example, the modeled patient journey network graph can model the various workflow events and patient encounters that occur throughout their journey along with associated clinical and non-clinical attributes using nodes connected by arcs (also referred to as edges) that capture the relationships between the attributes and the patient pathway. In this regard, the journey modeling component 204 can connect highly heterogenous patient flow data 118 from various in a graph structure that captures the journey of the patient, the encounters and events for the patient, time lapse of the events and patient pathway from one department/unit/bed to the other, and clinical and non-clinical attributes that influence movement of the patient between units/departments/beds. For example, such graphs structures can provide for learning that patients with certain admitting diagnosis, imaging scans and procedure codes move from the emergency department to a surgical suite or a surgical intensive care unit. In this regard, graph algorithms provide a means to understand, model and predict very complex dynamics such as flow of patients in a hospital with varying conditions and pathways.

Figure 4:
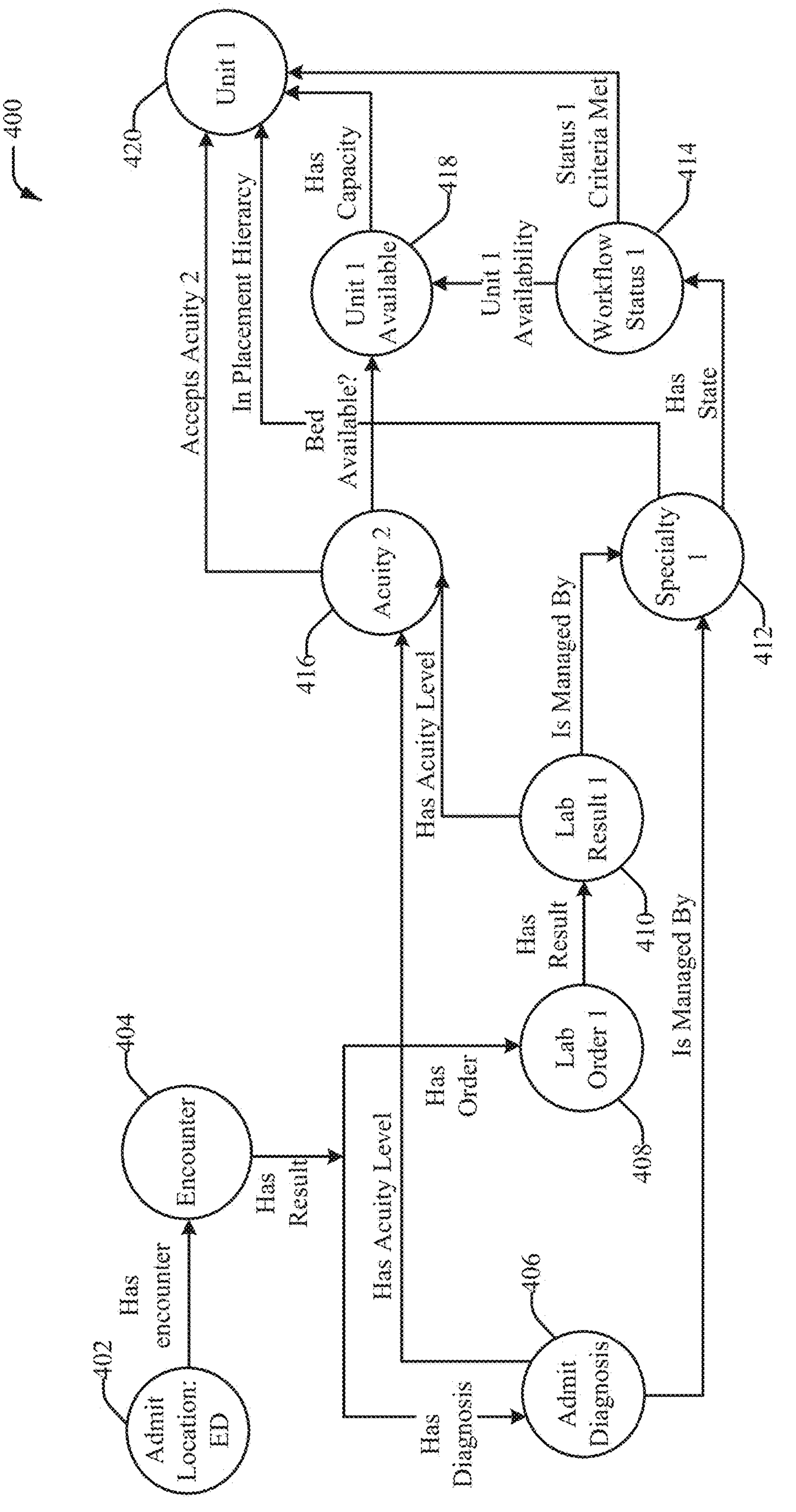
FIG. 4 presents example patient journey data modeled as a heterogenous network graph in accordance with one or more embodiments described herein.

FIG. 4 presents example patient journey data modeled as a heterogenous network graph 400 in accordance with one or more embodiments described herein. As shown in FIG. 4, the journey modeling component 204 can extract various patient journey attributes and relationships between those attributes from the patient flow data 118 and model them using nodes (represented by circles) and arcs (represented by the directional arrows connecting the nodes). In particular, the network graph 400 defines a complex network consisting of nodes and arcs that denotes a variety of patient, workflow, hospital data and relationships extracted from the patient flow data 118. For instance, in this example, the node 402 represents the admission location of the patient (e.g., the emergency department, ED), node 404 represents a clinical encounter (e.g., a clinical evaluation, a procedure, a diagnosis evaluation, etc.), node 406 represents an admission diagnosis, node 408 represents a lab ordering event, node 410 represents a reception of lab results event, node 412 represents a specialty assignment, node 414 represents a workflow status report, node 416 represents an acuity level assignment, node 418 represents a reported availability in unit 1, and node 420 represent movement of the patient into the available unit 1. The arcs between the nodes identify the relationships between the nodes.

The complexity of the graph structure can be modified depending on the questions that need to be answered. However, when a large number of patient data is captured in these graph type structures, patterns tend to emerge that can then be used to ascertain the likely future states of the patient depending on the number of arcs that flow from a given node to adjacent nodes.

With reference again to FIGS. 2 and 4, in various embodiments, the patient journey graphs (e.g., network graph 400 and the like) can be generated by the journey modeling component 204 for respective patients at the medical facility in real-time as new information for respective patients is received in the patient flow data 118. For example, the journey modeling component 204 can begin building a network graph for a patient at the time the patient is admitted or otherwise a case is opened for the patient. The journey modeling component 204 can further continue growing and building the graph over the course of their journey as new events and conditions arise are reported in the patient flow data 118. In the embodiment shown in FIG. 2, the journey graph data 206 represents the patient journey graphs that are generated by the journey modeling component 206. This journey graph data 206 may further be added to the historical patient flow data 116 and used to facilitate census forecasting model development and/or model training/updating.

In one or more embodiments, the patient flow component 102 can employ various machine learning techniques to learn patient flow patterns from patient journey network graphs to learn potential inpatient destinations depending on a variety of clinical and non-clinical attributes and estimate future census for inpatient units. For example, in some implementations, the patient flow component 102 can employ these graph structures to infer the next destination (e.g., next node) for a patient given a current snapshot of their journey by using one or more label propagation algorithms. In this regard, there are many algorithms available for inferencing the next node but label propagation algorithms which uses neighborhood majorities as a means of inferencing clusters is extremely fast and can scale linearly with the number of nodes. This extremely fast cluster inferencing algorithm known as label propagation can be used by the patient flow component 102 to estimate the future state and destination of the patients with current patient flow information. This allows the patient flow component 102 to learn the relevant features and their relationships that then be fed into the census forecasting models to improve the accuracy of census forecast. For example, by using label propagation through the patient graphs, the patient flow component 102 can narrow down the potential solutions (e.g., input variables) and can then be fed into census forecasting models to improve the accuracy of census forecast. In some embodiments, the patient flow component 102 can perform label propagation at different epochs or time intervals during training. The same conditions can further be replicated when applying the forecasting models for census prediction at runtime. Preliminary experiments on some units have resulted in census forecast accuracy being higher when there is no blocking of beds.

Figure 5:
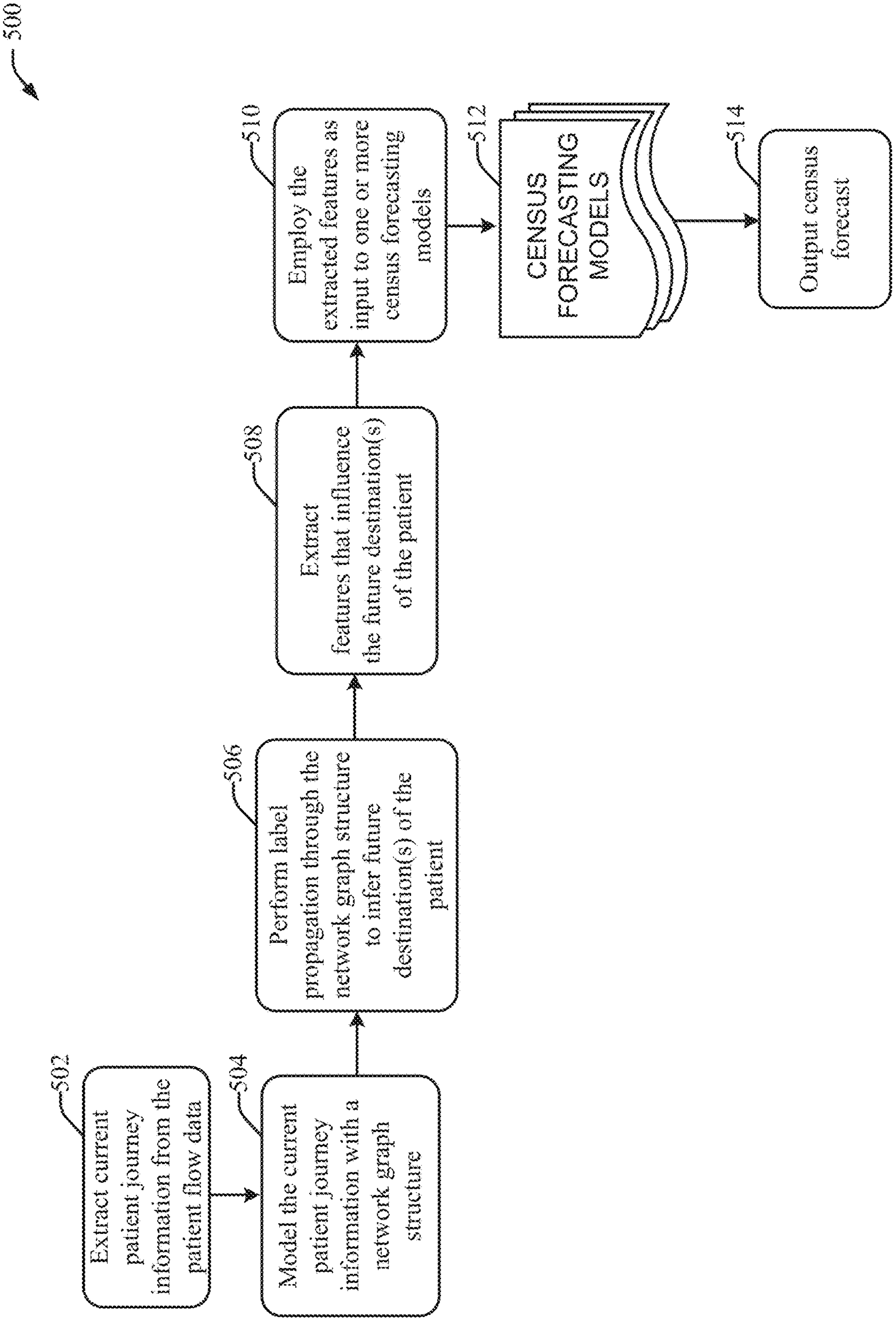
FIG. 5 presents a high-level flow diagram of an example method for employing patient journey data modeled as a heterogenous network graph to facilitate forecasting patient census data in accordance with one or more embodiments described herein.

FIG. 5 presents a high-level flow diagram of an example method 500 for employing patient journey data modeled as a heterogenous network graph to facilitate forecasting patient census data in accordance with one or more embodiments described herein. With reference to FIGS. 2 and 5, method 500 includes various processing steps that can be performed by the forecasting component 101 using journey modeling component 204, patient flow component 102 and patient census component 106. In accordance with method 500, at 502, the journey modeling component can extract current patient journey information from the patient flow data 118. At 504, the journey modeling component can model the current patient journey information with a network graph structure. At 506, patient flow component 102 can perform label propagation through the network graph structure to infer one or more possible future destinations of the patient. At 508, the patient flow component 102 can extract features that influence the one or more future destinations of the patient. At 508, the patient census component 106 can employ the extracted features as input to one or more census forecasting models 512 and output the corresponding census forecast at 514.

Figure 6:
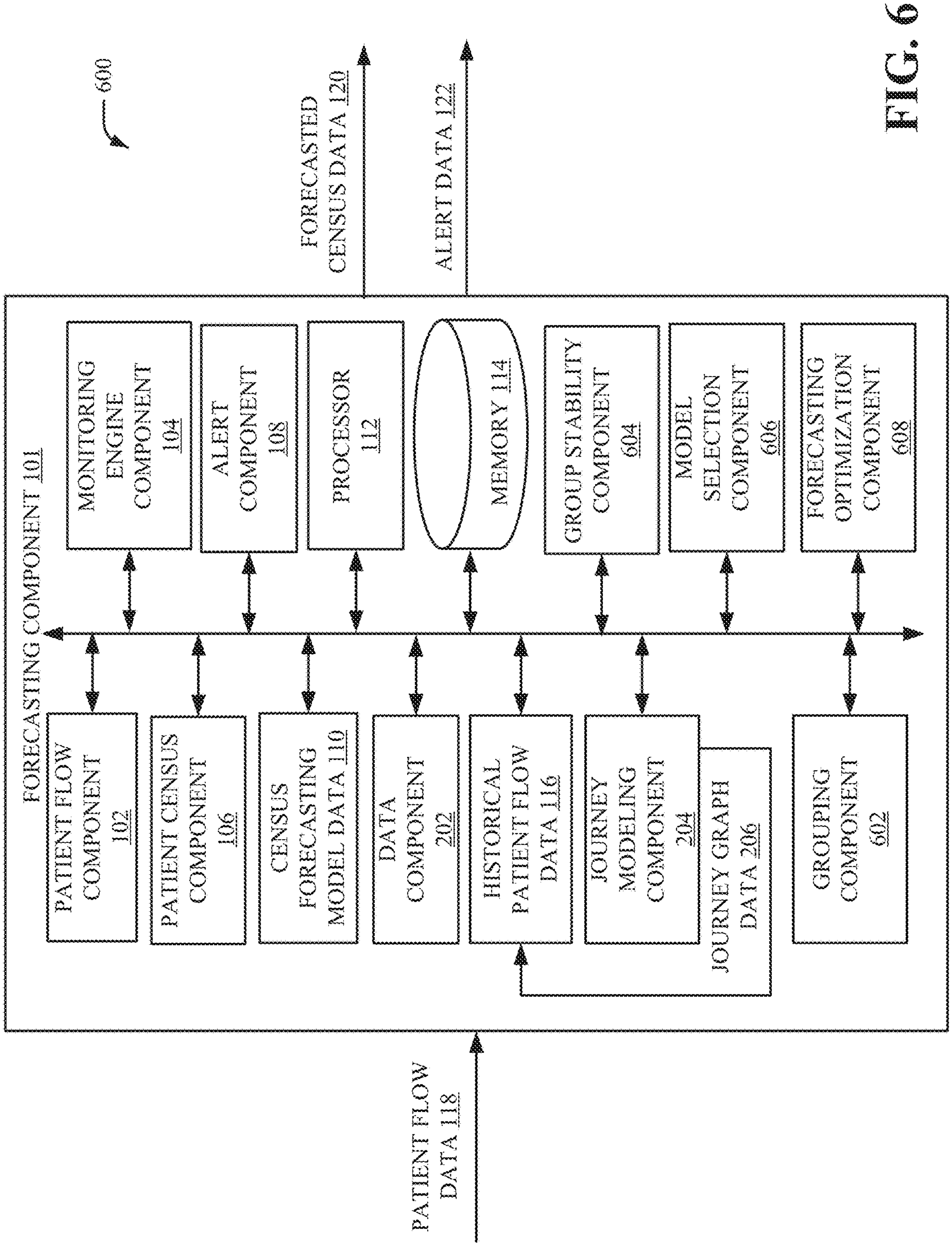
FIG. 6 illustrates a high-level block diagram of yet another example forecasting component, in accordance with one or more embodiments described herein.

FIG. 6 illustrates a non-limiting implementation of a system 600 in accordance with various aspects and implementations of this disclosure. System 600 can include same or similar component as system 200 with the addition of grouping component 602, group stability component 604, model selection component 606 and forecasting optimization component 608 to the forecasting component 101. Repetitive description of like elements employed in other embodiments described herein is omitted for sake of brevity.

System 600 facilitates modeling patient flow dynamics and generating forecasted census data 120 for a variety of different groupings of beds associated with an inpatient medical facility. For example, hospitals often group units logically known as cohorts within a hospital or a hospital network for variety of reasons (e.g., physician assignments, staffing assignments etc.). Hence, it is often important to provide accurate census forecasting regarding expected occupancy levels at the individual unit level as well as the cohort level.

A used herein, a bed cohort (or simply cohort), refers to a grouping of beds associated with a medical facility based on one or more grouping factors. The grouping factor can vary. For example, in some implementations, the grouping factor can be based association of the beds with a specific inpatient unit or group of two or more units. Thus, a bed cohort may include a single unit, all units at the medical facility, or a select grouping of two or more units at the medical facility.

The grouping factor can also be based on various other criteria associated with the beds, such as but not limited to, bed type, acuity level, service type/level, service line, location, bed mobility, and so on. With these embodiments, a bed cohort may include a subset of beds included in a single unit, as well as beds included in disparate units. For example, inpatient medical facilities can apply different rules and policies for placing patients in beds based on the type of medical service needed by the patient and type of bed needed by the patient in association with provision of the medical service to the patient. These rules and policies can control for example, where a patient can be treated, when the patient should be treated, who can treat the patient, medical supplies needed for treating the patient, protocols for treating the patient, and the like. For example, most hospitalizations involve one or more procedures, which can range from simple vaccinations to complex surgical procedures. Different types of beds are used for different types of procedures, situations and patient conditions and serve different purposes of treatments.

In some implementations in which a bed cohort includes two or more inpatient units, the patient census forecasting component 106 may employ separate forecasting models tailored to each of the different units to generate the expected census forecast (e.g., bed occupancy forecast) of each unit using the different models. The patient census forecasting component 106 may then aggregate the results of the respective models to generate the total expected occupancy level of all units in the group. However, there are several practical situations to be considered here. Often times, an inpatient unit may include a variety of beds that can accommodate patients of different acuity levels, service lines, hospital services, etc. Hence it would be very difficult to merely aggregate the forecast outputs of the individual unit models without losing some forecast accuracy. Said differently, when you aggregate the forecast outputs of separate models for separate units, the error also gets aggregated and forecast quality gets degraded.

To alleviate this compounding error issue and provide for forecasting census levels for a variety of different bed groupings, system 600 adopts a unique multilevel modeling approach. In accordance with this multilevel modeling approach, the historical census is calculated for every bed in the group and models are tailored for that group. The data at the grouped level is much less noisy and hence forecast accuracy is typically higher at the grouped level. This multilevel modeling method works well for census forecasts when the behavior of the beds and/or units in the group is highly correlated and the patient flow in these beds and/or units are stable. This multilevel modeling design accommodates for the hierarchy and data aggregation such that the number of models for the groups are kept to a minimum level.

In accordance with these embodiments, the grouping component 602 can define one or more groups of beds at the medical facility based on at least one grouping factor. For example, in some implementations, the grouping can be responsive to user input selecting/identifying a desired grouping factor or factors, such as a selected unit, a selected group of units, a selected bed type, a selected service line, a selected acuity level, a selected bed location (e.g., associated with a particular department, floor, building, etc. at the medical facility), or another bed attribute. In other implementations, the grouping component 602 can be configured to generate various different logical bed groupings based on predefined bed grouping factors and criteria for generating the bed groupings.

For each bed group, the grouping component 602 may further determine the relevant input parameters/features for input to one or more forecasting models that will be used to forecast the expected occupancy level of that bed grouping. For example, in some implementations, the grouping component 602 may direct the patient census component 106 to process the historical patient flow data 116 and/or the patient flow data 118 using one or more machine learning techniques to learn the input parameters that influence movement of patients into and out of the respective beds in the group based on analysis of the historical patient flow data 116. For instance, the patient census component 106 can learn patterns in patient journey network graphs generated by the journey modeling component 204 using label propagation and other machine learning techniques to determine the features that are most relevant for the bed group. Additionally, or alternatively, the input parameters for each bed grouping may be predefined. For example, in some implementations, the input parameters for all the census forecasting models may be the same.

The group stability component 604 further determines a measure of occupancy variability for the group based on historical census data for respective beds in the group, and the model selection component 606 selects one or more census forecasting models for the group based on the measure of occupancy variability. With this approach, forecasting component 101 considers the impact of grouping the beds on the variance of the group census. If the variance is higher, the model selection component 606 may select multiple machine learning models (potentially weak learners) and then combine them to provide more accurate forecasts. If the variance is lower, the model selection component 606 may potentially select one or fewer machine learning models and then provide forecast outputs. The tradeoff in terms of complexity and computational time comes from the variability of the grouped census. Such as approach can be used for a single unit, a group of units, or another bed grouping for a subset of beds same or different units.

The measure of occupancy variability can reflect a degree to which the occupancy level (i.e., census data) changes for the group over time and/or under different operating conditions of the medical facility. For example, assuming the group includes a single unit, and the historical census data for that unit reflects that the unit is consistently about 60% occupied (e.g., at about 60% bed occupancy) at any period of time daily. This occupancy rate reflects a highly stable occupancy rate. On the other hand, a highly unstable occupancy rate may be assumed if the historical census data for the unit reflects the occupancy levels for the unit vary from 0% occupancy to 100% occupancy at different time periods throughout the day (e.g., 24-hour period), and each day the occupancy levels for the unit change for different time periods. (e.g., every day the occupancy level at 10 am is unpredictable and may be anywhere from 0% occupancy to 100% occupancy). At the same time, a highly stable occupancy rate may be assumed if the historical census data for the unit reflects the occupancy level for the unit are consistently at around 50% every day from 6 am to noon, at about 80% every day from noon to 9 μm, and around 95% every day from 9 μm to 6 am. The measure of occupancy variability however can also be tailored to a specific time frame for the group in implementations in which different census forecasting models are developed for different time frames. For instance, in furtherance to the example, above, assume now that the occupancy rate for the unit from the hours of 6 am to noon everyday is consistently about 50%, yet from the hours of noon to 6 am every day the occupancy rate varies significantly (and is thus unpredictable). With this example, the occupancy variability for the unit from the hours of 6 am to noon may be considered low, while the occupancy variability for the unit for other time frames may be considered high.

In one or more embodiments, the group stability component 604 can determine the measure occupancy variability for the group based on the historical census data for each bead in the group. For instance, the historical patient flow data 116 can include information (e.g., determined/calculated by the data component 202) for each bed at the medical facility that measure its occupancy variability as a function of time. For example, with respect to a single bed, the occupancy variability data for the bed can indicate the percentage to which the bed is occupied or unoccupied each hour of the day, each day of the week. Additionally, or alternatively, the occupancy variability for the single bed may include a calculated occupancy variability value for the bed each hour of the day (determined as a function how consistently the bed is occupied or not at that hour of the day), and/or each day (e.g., determined as a function of how consistently the bed is occupied or not each day). Other time frames are envisioned. The group stability component 604 can further determine a measure of occupancy variability for the group of beds based on the combined historical occupancy variability rates of each bed in the group. The value or metric used to define the occupancy variability rate can vary.

Selection of the one or more forecasting models based on the occupancy variability of the group refers to selection of the number and/or type of machine learning models to be applied for forecasting the census level of the group (and/or of the group at a particular time fame/period) based on the current patient flow data 118. In this regard, various different types of machine learning algorithms/models exist and are being added to the AI field that have different strengths and weakness. For example, some suitable machine learning algorithms/models that can be used for the one census forecasting models can include but are not limited to: a nearest neighbor algorithm, a naïve Bayes algorithm, a decision tree algorithm, a boosting algorithm, a gradient boosting algorithm, a linear regression algorithm, a neural network algorithm, a k-means clustering algorithm, an association rules algorithm, a q-learning algorithm, a temporal difference algorithm, a deep adversarial network algorithm, or a combination thereof. Some of these models may be more conservative than another in association with forecasting future occupancy levels for a bed grouping.

Thus, in some embodiments, the patient census component 106 can apply a combination of two or more different types of census forecasting models to predict the census forecast for a bed group as weighted function of the outputs of the different models. As discussed below, with these embodiments, the forecasting optimization component 608 can employ one or more optimization techniques to determine the weights of the different models.

The model selection component 606 can be configured to select the number and type of the census forecasting models for the group based on the measure of occupancy variability for the group and defined selection criteria for the measure of variability. For example, in some implementations, the selection criteria can include one or more threshold values or ranges for the measure of variability, wherein each threshold value or range is coupled to a defined rule for the number and type of models to be applied. For instance, the selection criteria can instruct the model selection component 606 to select a single model of type A if the measure of variability is below a first threshold value, a model of type A and B if the measure of variability is between the first threshold value and a second threshold value, a model of type A, B and C if the measure of variability is between the second threshold value and a third threshold value, and so on. It should be appreciated that the model selection rules based on the measure of occupancy variability for the group can vary.

In some embodiments, the forecasting optimization component 608 (and/or the training component 802 discussed infra) can perform a parameter tuning process to tune one or more parameters or hyperparameters of the selected census forecasting model or models for the group. For example, the forecasting optimization component 608 can fine tune one or more parameters or hyperparameters of the model or models for the group based on the historical patient flow data in accordance with the model training and updating processes discussed infra.

In implementations in which two or more forecasting models are selected, the forecasting optimization component 608 can further determine appropriate weights for the respective models and combine the outputs of the respective models using the weights to generate a final census forecast for the bed group (or bed group at a specific time period). In some embodiments, the forecasting optimization component 608 can employ a non-convex optimization technique to estimate the weights of the different models based on the relative performance accuracy of the respective models (e.g., as observed during a model evaluation phase of the model training/development process discussed infra). For example, in one or more embodiments, the non-convex optimization technique can include a quadradic programming optimization technique in accordance with the following quadradic programming Equation 1, wherein where, MSE=Mean Square Error; Y1, Y2, . . . , Yk are the outputs from the models; and w1, w2, . . . , wk are the weights assigned to the model outputs.

$$\text{Min } MSE(w1Y1 + w2Y2 + \ldots + wkYk,\ Y) \qquad \text{Equation 1}$$
$$\sum wjkj = 1 = 1;\qquad .$$
$$wj \geq 0,\ \forall\ j = 1, \ldots, k,$$

Equation 1 is a quadratic programming problem. Since the constraints are linear, the convexity can easily be proved by computing the Hessian matrix of the objective function. Therefore, since a local minimum of a convex function on a convex feasible region is guaranteed to be a global minimum, the forecasting optimization component 606 can conclude that the optimal solution achieves global optimality.

In some implementations, the forecasting optimization component 606 may use Python's SciPy optimization library to solve this Equation 1. This library contains numerous algorithms for constrained and unconstrained optimization. Additionally, or alternatively, the forecasting optimization component 606 can employ a Sequential Least Squares Programming (SLSQP) algorithm (a special case of sequential quadratic programming) to determine the respective model weights.

In accordance with Equation 1, the mean squared error (MSE) is used to evaluate the model performance, which is a measure of difference between predicted and observed values. However, various other measures may be used by the forecasting optimization component 606 to evaluate the model performance.

With our approach, the forecasting optimization component 606 optimizes the census forecasting models using the tuned hyper parameters and then optimizes the ensemble weights. This reduces the need to iterate to find the best ensemble using a combination of weights and hyper parameters thereby reducing computational time. The patient census component 106 further applies the one or more tuned/optimized census forecasting models to the current patient flow data 118 for the medical facility to forecast an expected occupancy level for the group during one or more future periods of time.

Figure 7:
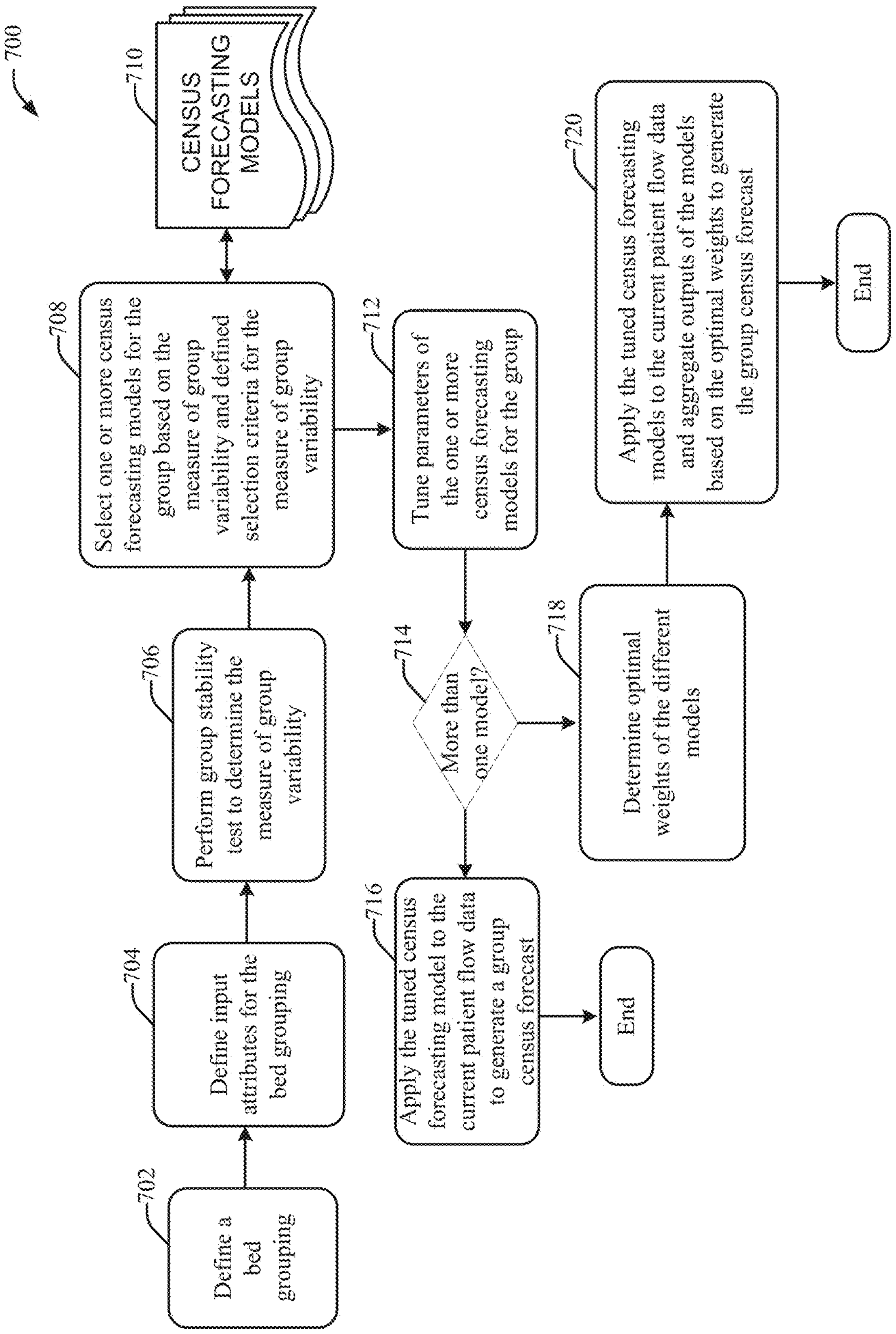
FIG. 7 presents a high-level flow diagram of an example multi-level modeling process for patient census forecasting in accordance with one or more embodiments described herein.

FIG. 7 presents a high-level flow diagram of an example multi-level modeling process 700 for patient census forecasting in accordance with one or more embodiments described herein. Process 700 provides an example method for forecasting patient census information for any grouping of beds at a medical facility. In accordance with process 700, at 702, the grouping component 602 may define a bed grouping. For example, the bed grouping may include all beds in a single unit, all beds in two or more selected units, a subset of beds in a single unit with one or more particular attributes (e.g., a selected bed type, service line, acuity level, mobility function, etc.), or a subset of beds included in two or more units with one or more particular attributes. At 704, the grouping component may further define (or apply predefined) input attributes for the bed grouping. At 706, the group stability component 604 performs a groups stability test to determine the measure of group occupancy variability. For example, the measure of group occupancy variability can be a general daily or weekly group variability measure and/or for a selected time frame (e.g., a particular hour or time period within the day), a particular day of the week (e.g., Saturday), or another time point. At 708, the model selection component 606 may select one or more census forecasting models 710 for the group based on the measure of group variability and defined selection criteria for the measure of group variability, wherein the number and/or type of the models selected varies based on the measure of group variability. The census forecasting models 710 can include a variety of different types of machine learning models (e.g., random forest, gradient boost, decision tree, etc.) from which the model selection component 606 may choose from. The model selection component 606 may be configured to select a single model of a first type (e.g., a strong learner type) if the measure of variability is low (e.g., relative to a defined threshold), and two or more models of different types if the measure of variability is high (e.g., relative to a defined threshold). In some embodiments, the census forecasting models 710 may include models that have been previously trained on the historical patient flow data 116 to generate census forecasts for one or more inpatient units and/or bed cohorts. Additionally, or alternatively, the initial model training and development of these ML into census forecasting models for a particular bed group can be carried out after selection at 708 and before parameter tuning at 712. Techniques for model training and development are discussed infra with reference to FIGS. 8 and 9. These census forecasting models 710 may be included in the census forecasting model data 110 or another suitable database accessible to the forecasting component 101.

Figure 8:
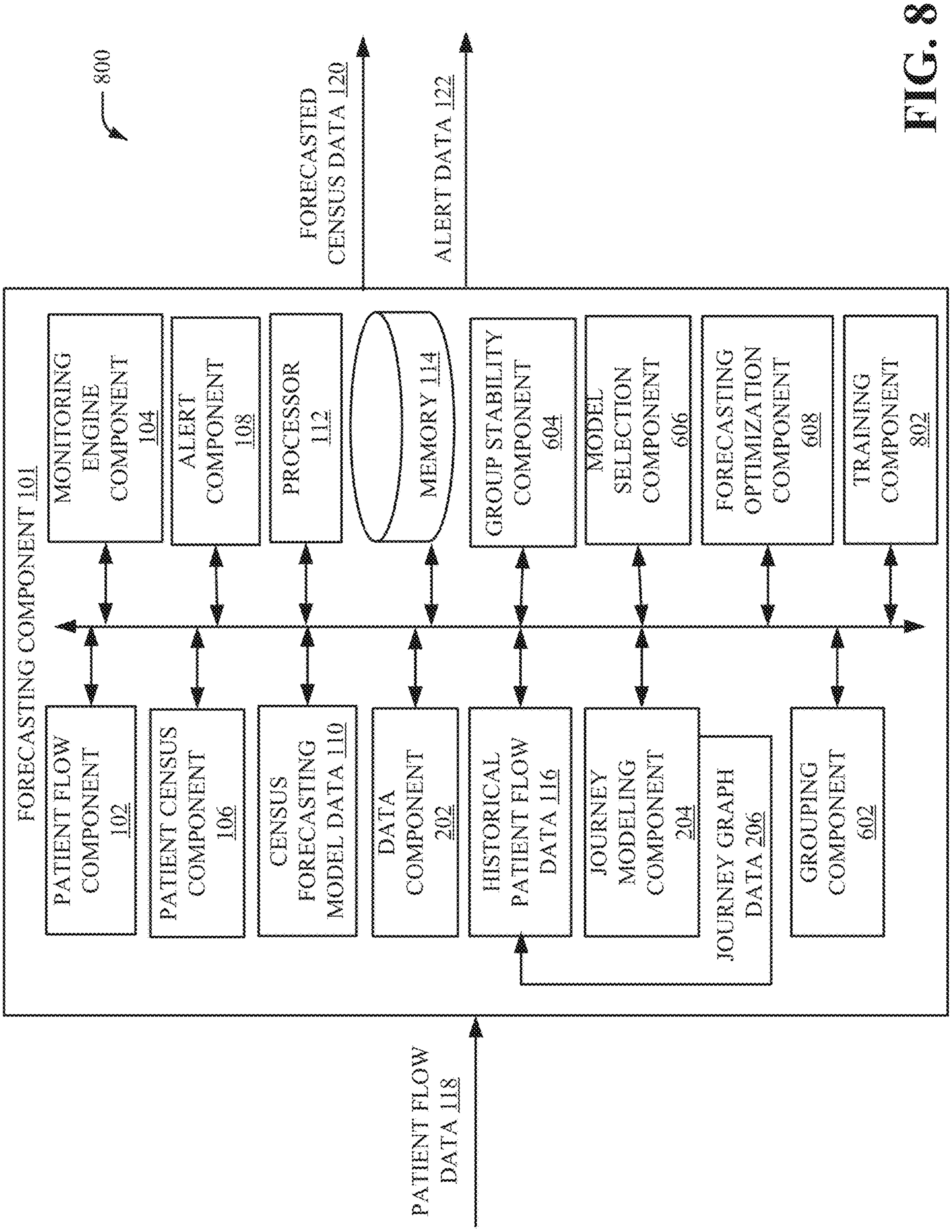
FIG. 8 illustrates a high-level block diagram of yet another example forecasting component, in accordance with one or more embodiments described herein.
Figure 9:
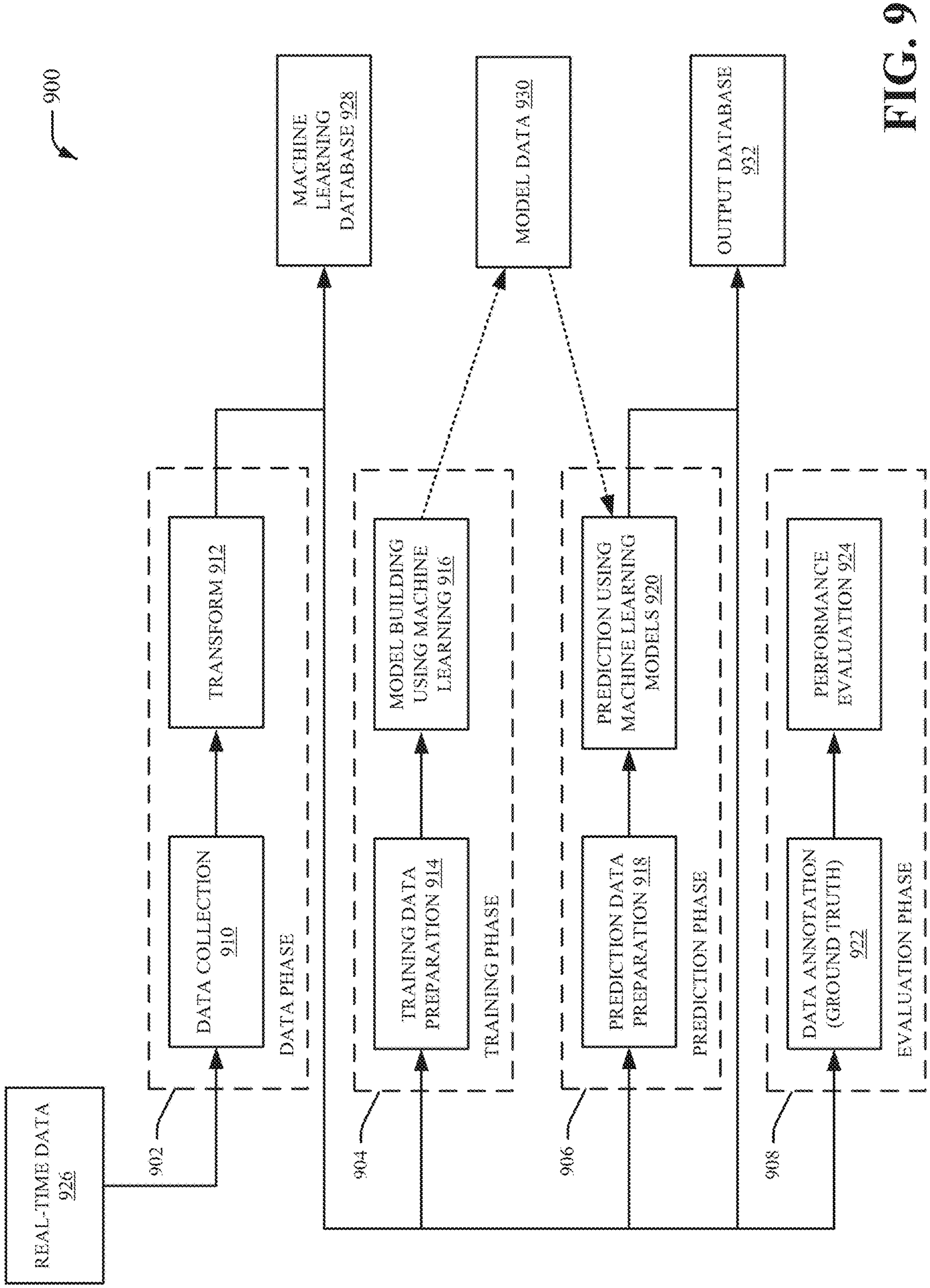
FIG. 9 illustrates an example system associated with a machine learning process for monitoring, predicting and/or alerting for census periods at a medical facility, in accordance with one or more embodiments described herein.

At 712, the forecasting optimization component 608 may tune one or more parameters (e.g., hyperparameters) of the one or more census forecasting models for the group using the historical patient flow data 116 for model training/tuning, model testing and model evaluation (as disused infra with reference to FIGS. 8 and 9). At 714, the forecasting optimization component 608 determines whether there is more than once census forecasting model for the group. If not, then at 716, the patient census component 106 can apply the tuned census forecasting model to the patient flow data (e.g., patient flow data 118) to generate a census forecast for the group. For example, the census forecast can indicate an expected number of patients to be placed (or have a placement request) for beds in the group at one or more future points or periods of time. However, there are two or more census forecasting models, then at 718, the forecasting optimization component 608 can determine the optimal weights of the different models using one or more optimization techniques as discussed above. At 720, the patient census component 106 may apply the tuned census forecasting models to the current patient flow data and aggregate the outputs of the census forecasting models based on the optimal weights to generate the group census forecast.

Referring now to FIG. 8, there is illustrated a non-limiting implementation of a system 800 in accordance with various aspects and implementations of this disclosure. System 800 can include same or similar component as system 600 with the addition of training component 802 to the forecasting component 101. Repetitive description of like elements employed in other embodiments described herein is omitted for sake of brevity.

The training component 802 can generate one or more machine learning models including the one or more census forecasting models. In this, regard, a machine learning model can extract dominant factors for a given medical inpatient unit and/or bed grouping (i.e., a bed component). A machine learning model can additionally or alternately extract time series information such as trends, seasonality trends, intervals and/or cycles that affect census in a given medical inpatient unit and/or bed grouping. A machine learning model can additionally or alternately estimate duration of patients to move from a given medical inpatient unit to another medical inpatient unit and/or bed grouping. In an embodiment, the training component 802 can generate a first machine learning model for the first machine learning process associated with learning the one or more patterns in the historical patient flow data 116 (e.g., including the journey graph data 206) and/or the current patient flow data 118. The training component 802 can generate the first machine learning model for the first machine learning process based on the historical patient flow data 116 and/or the current patient flow data 118. For example, the training component 802 can generate the first machine learning model for the first machine learning process based on the patient data, the operations data and/or the resource data. Additionally, or alternatively, the training component 802 can generate a second machine learning model for the second machine learning process associated with detecting the one or more abnormalities with respect to the one or more patterns in the current patient flow data 118. The training component 802 can generate the second machine learning model for the second machine learning process based on the historical patient flow data 116. For example, the training component 802 can generate the second machine learning model for the second machine learning process based on the patient data, the operations data and/or the resource data.

The training component 802 can also tune one or more parameters for a machine learning model (e.g., a census forecasting model) based on an evaluation of the forecasted census data 120. For example, the training component 802 can tune one or more parameters for the first machine learning model associated with the first machine learning process based on an evaluation of the forecasted census data 120. Additionally, or alternatively, the training component 802 can tune one or more parameters for the second machine learning model associated with the second machine learning process based on an evaluation of the forecasted census data 120. In an embodiment, the training component 802 can learn one or more patters associated with the historical patient flow data 116. The training component 802 can also estimate patient flow relationships (e.g., complex patient flow relationships) associated with the historical patient flow data 116. The training component 802 can employ the estimated patient flow relationships to tune tunes one or more parameters for a census forecasting model for a particular inpatient unit and/or bed grouping.

Referring to FIG. 9, there is illustrated a non-limiting implementation of a system 900 in accordance with various aspects and implementations of this disclosure. Repetitive description of like elements employed in other embodiments described herein is omitted for sake of brevity.

The system 900 includes a data phase 902, a training phase 904, a prediction phase 906 and/or an evaluation phase 908. The data phase 902, the training phase 904, the prediction phase 906 and/or the evaluation phase 908 can be executed during a machine learning process. For example, the data phase 902, the training phase 904, the prediction phase 906 and/or the evaluation phase 908 can be respective phases of a machine learning process. The data phase 902 can include a step 910 associated with data collection. The data phase 902 can additionally or alternatively include a step 912 associated with a transform. The training phase 904 can include a step 914 associated with training data preparation. The training phase 904 can additionally or alternatively include a step 916 associated with model building using machine learning. The prediction phase 906 can include a step 918 associated with prediction data preparation. The prediction phase 906 can additionally or alternatively include a step 920 associated with prediction using machine learning models. The evaluation phase 908 can include a step 922 associated data annotation (ground truth). The evaluation phase 908 can additionally or alternatively include a step 924 associated with performance evaluation.

With reference to FIGS. 8 and 9, in an embodiment, real-time data 926 can be provided to the data phase 902. For instance, the step 910 of the data phase 902 can perform data collection to collect the real-time data 926. The real-time data 926 can include or correspond to the patient flow data 118. For example, the real-time data 926 can include medical data, sensor data, process data (e.g., process log data), monitoring data, maintenance data, parameter data, measurement data, performance data, textual data, audio data, image data, video data, machine data, asset data, equipment data, medical device data, metadata, real-time data, historical data and/or other data. Furthermore, the real-time data 926 can be encoded data, processed data and/or raw data. For example, in some implementations, the real-time data 926 may include patient journey network graphs generated modeled by the journey modeling component 204 that tracks respective patient journeys at the medical facility in real-time (e.g., from admittance to discharge). The step 912 of the data phase 902 can transform the real-time data 926 into data for use by the training phase 904 of the machine learning process, the prediction phase 906 of the machine learning process, and/or the evaluation phase 908 of the machine learning process. For example, the step 912 of the data phase 902 can transform the real-time patient flow data 118 into historical patient flow data 116 over time. In another embodiment, the data generated by the step 912 (e.g., the transformed real-time data and/or the historical patient flow data 116) can be stored in a machine learning database 928.

In another embodiment, the step 914 of the training phase 904 can employ the data (e.g., the historical patient flow data 116) stored in the machine learning database 928 to prepare training data for machine learning. The step 916 of the training phase 904 can employ the training data to build a model using machine learning. For example, the step 916 of the training phase 904 can employ the training data to build a machine learning model. Model data 930 can, for example, correspond to the machine learning model generated at step 916, that is, a census forecasting model for a particular inpatient unit and/or bed grouping for a particular future point or period of time. For example, the model data 930 can correspond to the census forecasting model data 110. The model data 930 (e.g., the machine learning model) can be associated with one or more patterns in the real-time data 926 related to a set of patient identities and a set of operations associated with a set of medical inpatient units. Additionally or alternatively, the model data 930 (e.g., the machine learning model) can be associated with one or more abnormalities associated with the one or more patterns in the real-time data 926. In yet another embodiment, the step 918 of the prediction phase 906 can employ the data stored in the machine learning database 928 to prepare prediction data for machine learning. The step 920 of the prediction phase 906 can employ the prediction data to predict using machine learning models. For example, the step 920 of the prediction phase 906 can employ the prediction data from step 918 and/or the model data 930 to predict patient census data associated with a prediction for a total number of patient identities in the particular medical inpatient unit and/or bed grouping during a period of time. The forecasted census prediction determined by the step 920 can be stored in an output database 932. In yet another embodiment, the step 922 of the evaluation phase 908 can employ the data stored in the machine learning database 928 for data annotation. For example, the step 922 of the evaluation phase 908 can employ the data stored in the machine learning database 928 to determine ground truth accuracy of the prediction generated by the step 920. The step 924 of the evaluation phase 908 can evaluate performance of the machine learning process based on the data annotation from the step 922. For example, the step 924 of the evaluation phase 908 can employ one or more metrics to determine classification accuracy of the prediction determined by the step 920 of the prediction phase 906.

Figure 10:
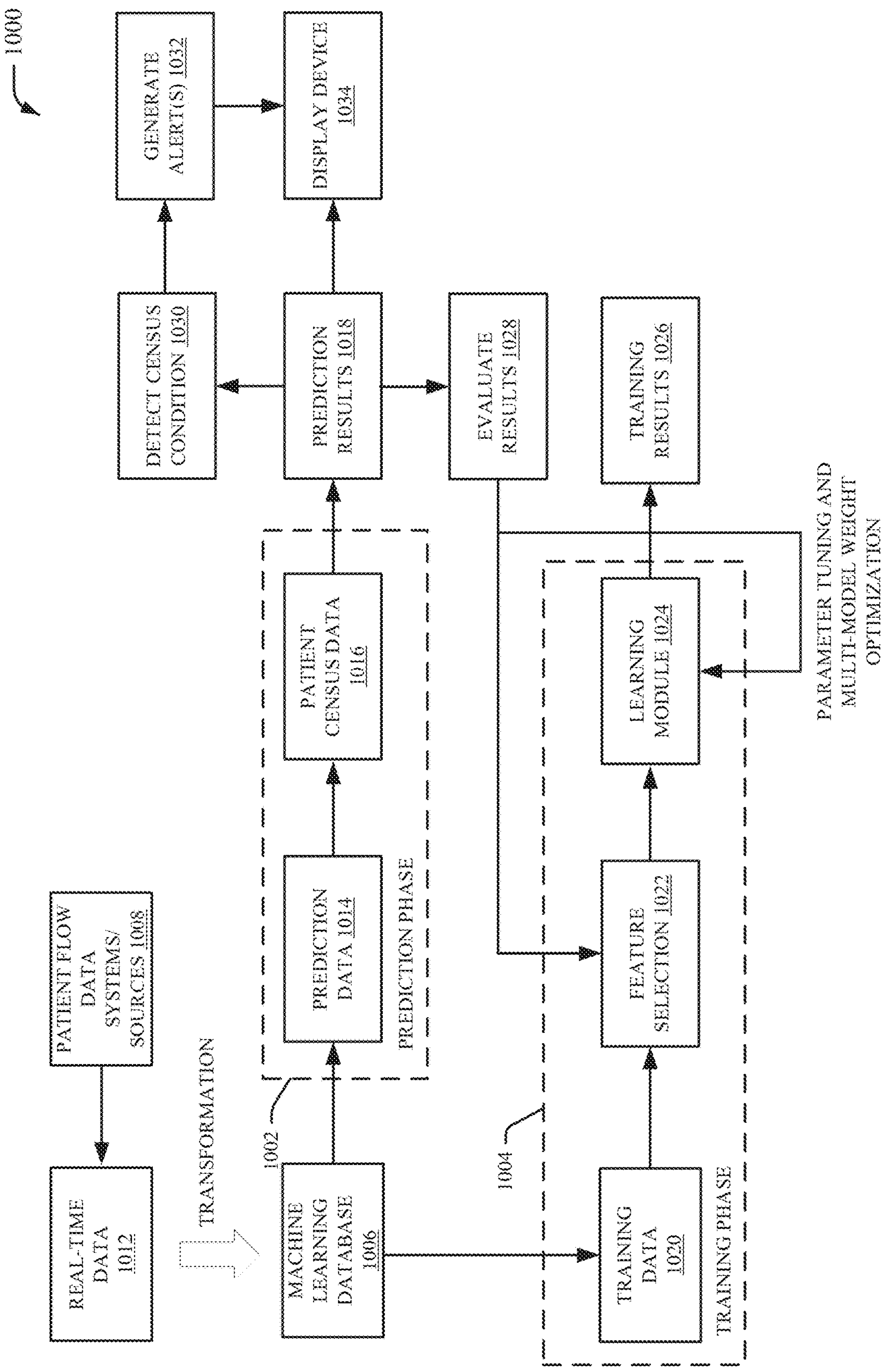
FIG. 10 illustrates an example system associated with another machine learning process for monitoring, predicting and/or alerting for census periods at a medical facility, in accordance with one or more embodiments described herein.

Referring to FIG. 10, there is illustrated a non-limiting implementation of a system 1000 in accordance with various aspects and implementations of this disclosure. Repetitive description of like elements employed in other embodiments described herein is omitted for sake of brevity.

With reference to FIGS. 8-10, the system 1000 includes a prediction phase 1002 and a training phase 1004 for a machine learning process. The prediction phase 1002 and/or the training phase 1004 can employ data from a machine learning database 10010. The machine learning database 1006 can receive real-time data 1012 corresponding to the current patient flow data 118 from various patient flow data systems/sources 1008 (e.g., a patient EHR system 306, patient monitoring systems/device 308, a bed management system 310, an imaging system 312, a laboratory system 314, facility operations tracking systems 316, and/or various other medical facility sources systems 318). The real-time data 1012 can be aggregated and stored in the machine learning database 1006 as it received over time as historical patient flow data 116. The real-time data 1012 can undergo a transformation into the data stored in the machine learning database 1006 for machine learning. Based on the data stored in the machine learning database 1006, the prediction phase 1002 can generate prediction data 1014. The prediction phase 1002 can also employ the prediction data 1014 to generate patient census data 1016. For example, the prediction data 1014 can correspond to relevant extracted features/feature values from the patient flow data included in the machine learning database 1006 for input into one or more patient census forecasting models to generate the patient census data 1016. In this regard, the predication phase 1002 can involve selecting (e.g., by the model selection component 606 and/or the patient census component 106) one or more previously trained/developed census forecasting models as provided by the census forecasting model data 110 for generating the patient census data 1016, and applying the one or more selected models to the prediction data (e.g., by the patient census component 106) to generate the patient census data 1016. In some implementations, the prediction phase 1002 can also encompass one or more steps of process 700. For example, the prediction phase 1002 may involve determining/defining a bed group for which a census prediction is desired, evaluating the stability of the bed grouping, selecting the appropriate number and/or type of forecasting models based on the stability of the bed grouping, tuning one or more parameters of the model for the bed grouping, applying the forecasting model or models to the prediction data 1014 and aggregating the results two or more models based on the optimal weights determined for the respective models. In this regard, the patient census data 1016 can provide a prediction for patient census in associated with a particular inpatient unit and/or bed grouping at or during a future point or period of time. The patient census data 1016 can be provided a prediction results 1018.

Additionally, or alternatively, based on the data stored in the machine learning database 1006, the training phase 1004 can generate training data 1020. For example, the training data 1020 can comprise sets of historical patient flow data reflecting the patient flow dynamics and dynamic state of the medical facility operations that are relevant to the patient flow dynamics at one or more past points/periods of time. For instance, in some implementations, the historical sets of the patient flow data can correspond to historical patient flow data captured over the course of each past day, each past hour, each past week, each past month and so on. Feature selection 1022 of the training phase 1004 can employ the training data 1020 for selecting one or more features to generate a machine learning model. A learning module 1024 of the training phase 1004 can be employed to build one or more machine learning models based on the feature selection 1022. Training results 1026 of the training phase 1004 can be generated by the learning module 1024. In an embodiment, evaluate results 1028 can be employed to evaluate the prediction results 1018. The evaluate results 1028 can be employed by the feature selection 1022 of the training phase 1004. Additionally, or alternatively, evaluate results 1028 can be employed for parameter tuning and/or multi-model weight optimization associated with the learning module 1024. With these embodiments, the learning module 1024 can include or correspond to the forecasting optimization component 608. For example, the evaluate results 1028 can be employed to tune one or more parameters of a census forecasting model or models generated by the learning module 1024. In implementations in which two or more forecasting models are selected for forecasting the patient census, the evaluate results 1028 can also be employed to determine the optimal weights of the respective models for aggregating their census output to generate a final census forecast. In some embodiments, the training phase 1004 may involve 700. For example, the training phase 1004 may involve determining/defining a bed group for which a census prediction is desired, evaluating the stability of the bed grouping, selecting the appropriate number and/or type of forecasting models for training/tuning/optimization based on the stability of the bed grouping, applying the forecasting model or models to the training data 1020, and performing the parameter tuning and weight optimization process based on evaluation of the results 1028.

The detect census condition 1030 can be employed to detect a condition associated with the patient census data 1016/prediction results 1018. For instance, the detect census condition 1030 can be employed (e.g., by the monitoring engine 104 and/or the alert component 108) to detect whether the patient census data 1016 satisfies a defined criterion associated with a defined threshold level (e.g., the detect census condition 1030 can be employed to detect an extreme census condition). In another example, assume the forecasted patient census data 1016 indicates an expected number of patients to be placed or need placement in a bed of a particular unit and/or bed group at a future period of time (e.g., one hour from the current time, two hours from the current time, 6 hours from the current time, 24 hours from the current time, 48 hours from the current time, etc.). The detect census condition 1030 can correspond to determining whether the expected number is normal, high, or low (e.g., relative to a defined threshold). For instance, the detect census condition 1030 can involve determining whether the expected number is beyond a configurable limit for the medical facility, such as whether the expected number exceeds a capacity of the unit and/or bed grouping, whether the expected number indicates a high capacity and the need for reassignment of additional resources (e.g., staff, medical supplies, etc.) to the unit/bed grouping, and so on. Based on the detected census condition, generate alert(s) 1032 can generate one or more alerts for a user interface. For example, one or more alerts can be generated for a user interface in response to a determination that the patient census data 1016 satisfies the defined criterion. Furthermore, the one or more alerts can be presented on a display device 1034.

Figure 11:
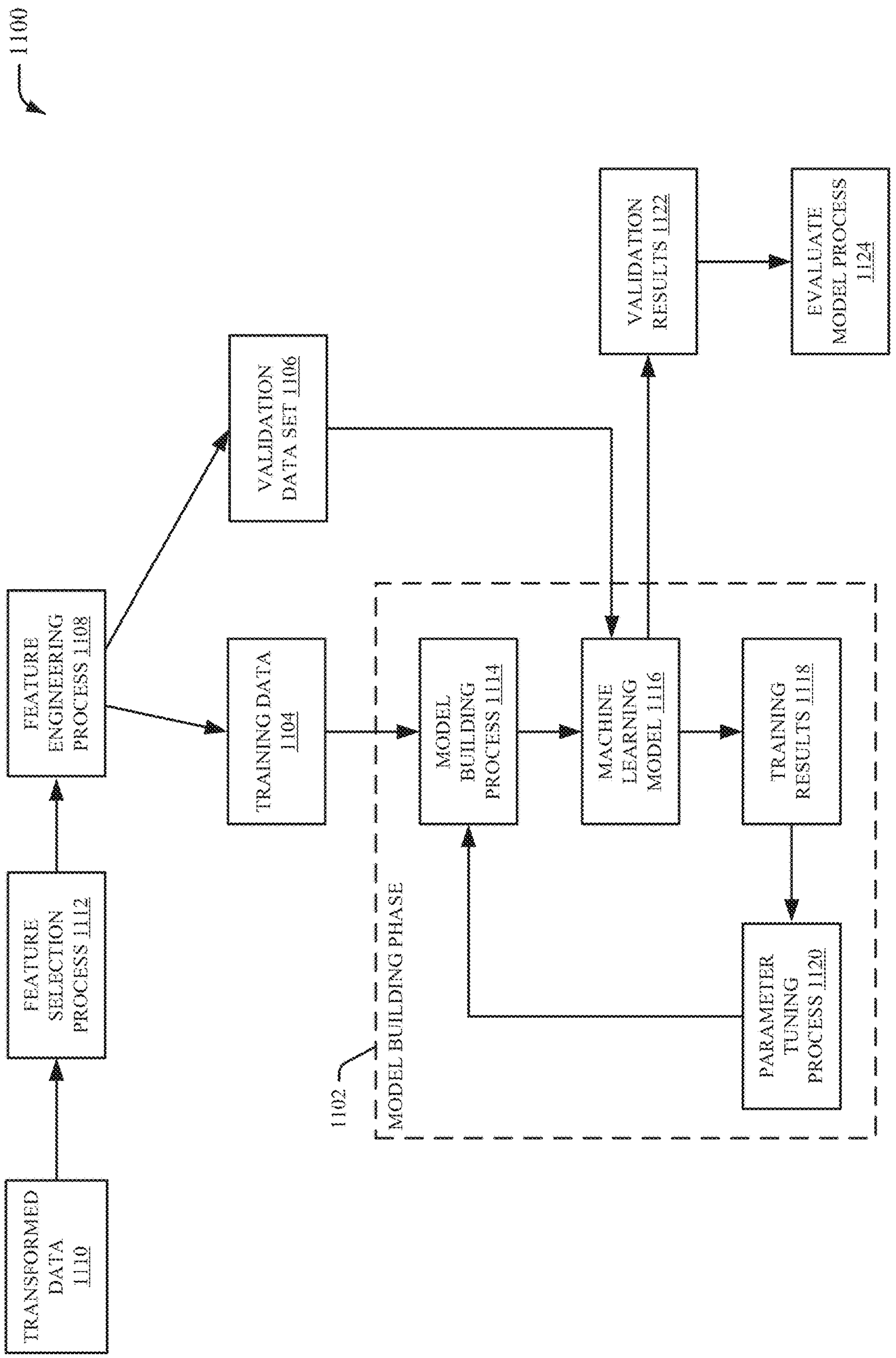
FIG. 11 illustrates an example system associated with yet another machine learning process for monitoring, predicting and/or alerting for census periods at a medical facility, in accordance with one or more embodiments described herein.

Referring to FIG. 11, there is illustrated a non-limiting implementation of a system 1100 in accordance with various aspects and implementations of this disclosure. Repetitive description of like elements employed in other embodiments described herein is omitted for sake of brevity.

The system 1100 includes a model building phase 1102 for a machine learning process. The model building phase 1102 can employ training data 1104 and/or validation data set 1106. In an embodiment, training data 1104 and/or validation data set 1106 can be generated via a feature engineering process 1108. The feature engineering process 1108 can employ a machine learning process to generate the training data 1104 and/or validation data set 1106. For example, the feature engineering process 1108 can employ a training phase of a machine learning process to generate the training data 1104. Additionally, or alternatively, the feature engineering process 1108 can employ a prediction phase of a machine learning process to generate the validation data set 1106. In certain embodiments, transformed data 1110 (e.g., transformed data 1110 stored in a machine learning database) can be employed by a feature selection process 1112. The transformed data 1110 can be, for example, a transformed version of real-time data and/or a transformed version of patient flow data. The feature selection process 1112 can select one or more features to build one or more machine learning models via the feature engineering process 1108. For example, in some embodiments, the feature selection process 1112 can involve employing patient journey graphs to learn and extract attributes and/or relationships between the attributes that influence flow dynamics to a particular unit and/or bed of a bed grouping. In another embodiment, the model building phase 1102 can include a model building process 1114. The model building process 1114 can build one or more machine learning models (e.g., census forecasting models) associated with the transformed data 1110. For example, the model building process 1114 can build a machine learning model 1116 based on the training data 1104 and/or the validation data set 1106. The machine learning model 1116 can be associated with one or more patterns in the transformed data 1110 related to a set of patient identities and a set of operations associated with a set of medical inpatient units. Additionally, or alternatively, the machine learning model 1116 can be associated with one or more abnormalities associated with the one or more patterns in the transformed data 1110. In an aspect, the machine learning model 1116 can provide training results 1118. Furthermore, a parameter tuning process 1120 can be performed based on the training results 1118 to tune one or more parameters for the model building process 1114. In another aspect, the machine learning model 1116 can provide validation results 1122 to validate the machine learning model 1116. The validation results 1122 can be employed by an evaluate model process 1124 to evaluate one or more metrics for the machine learning model 1116.

Figure 12:
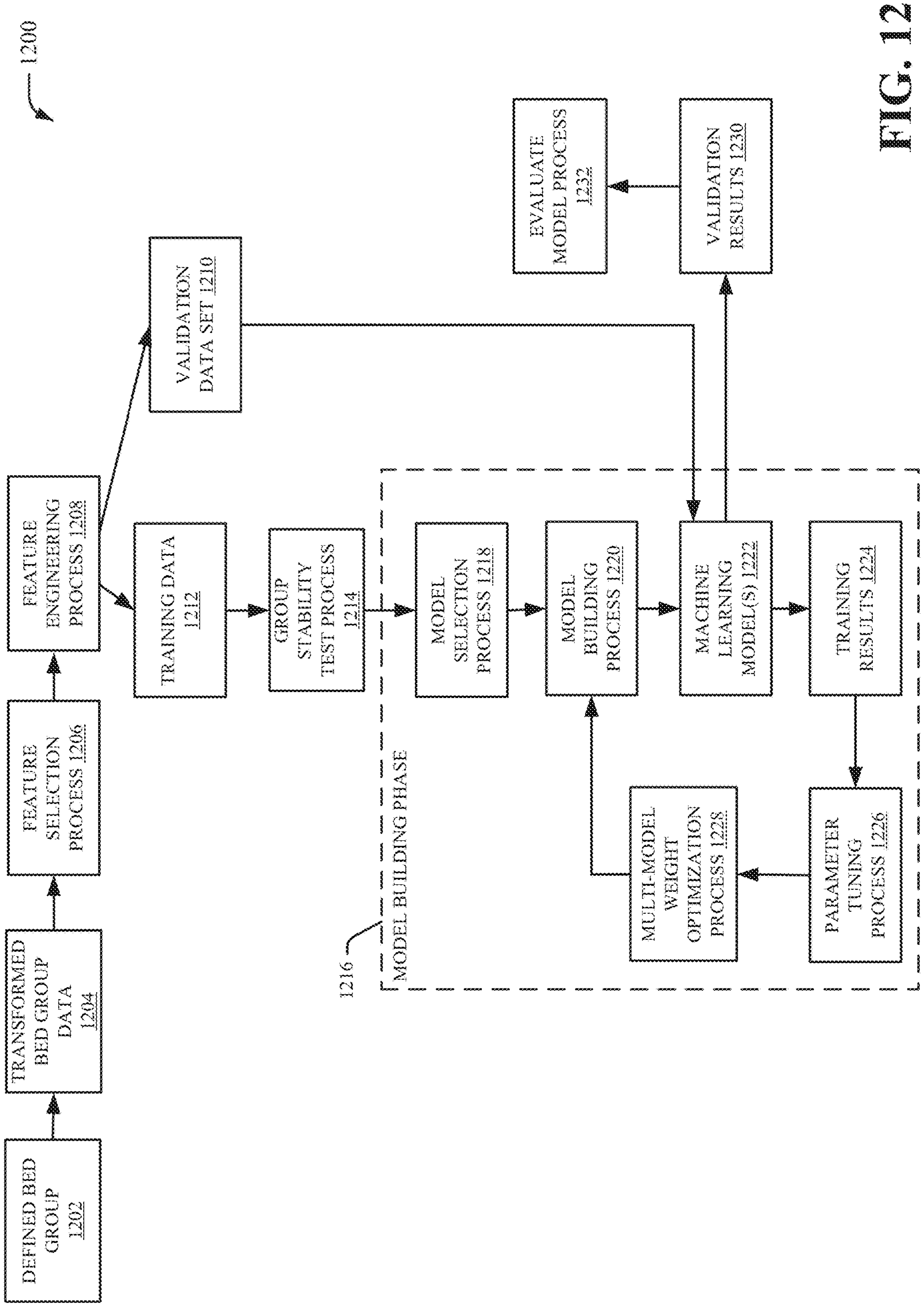
FIG. 12 illustrates an example system associated with yet another machine learning process for monitoring, predicting and/or alerting for census periods at a medical facility, in accordance with one or more embodiments described herein.

Referring to FIG. 12, there is illustrated a non-limiting implementation of a system 1200 in accordance with various aspects and implementations of this disclosure. Repetitive description of like elements employed in other embodiments described herein is omitted for sake of brevity.

The system 1200 includes a model building phase 1216 for building one or more machine learning models 1222, such as one or more census forecasting models. The model building phase 1216 can employ training data 1212 and/or validation data set 1210. In an embodiment, training data 1212 and/or validation data set 1210 can be generated via a feature engineering process 1208. The feature engineering process 1208 can employ a machine learning process to generate the training data 1212 and/or validation data set 1210. For example, the feature engineering process 1208 can employ a training phase of a machine learning process to generate the training data 1212. Additionally, or alternatively, the feature engineering process 1208 can employ a prediction phase of a machine learning process to generate the validation data set 1210. In accordance with system 1200, the training data 1212 and the validation data set 1210 can be used to train and/or tune one or more census forecasting models for a bed grouping. In this regard, with reference to FIGS. 8 and 12, the transformed bed group data 1204 can be generated from historical patient flow data 116 for a defined bed group 1202. In certain embodiments, transformed bed group data 1204 (e.g., transformed bed group data 1204 stored in a machine learning database or another suitable structure) can be employed by a feature selection process 1206. The feature selection process 1206 can select one or more features to build one or more machine learning models 1222 (i.e., one or more bed group census forecasting models) via the feature engineering process 1208. For example, in some embodiments, the feature selection process 1212 can involve employing patient journey graphs to learn and extract attributes and/or relationships between the attributes that influence flow dynamics to the defined bed group 1202.

In accordance with system 1200, the group stability process 1214 can involve determining the historical census variability of the group using historical census data for the respective beds in the group (e.g., by the group stability component 604). The model building phase 1216 can further include a model selection process 1218 wherein the model selection component 606 selects one or more machine learning models training/tuning into the census forecasting models for the group based on the measure of group variability. As discussed with reference to FIGS. 6 and 7, the number and type of machine learning models selected can vary based on the measure of group variability. The model building phase 1202 can include a model building process 1220. The model building process 1220 can build one or more machine learning models (e.g., group census forecasting models) associated with the transformed bed group data 1204. For example, the model building process 1114 can build the selected machine learning model or models 1222 based on the training data 1212 and/or the validation data set 1210. In an aspect, the machine learning model(s) 1222 can provide training results 1224. In addition, a parameter tuning process 1226 can be performed based on the training results 1224 to tune one or more parameters for the model building process 1220. For example, the parameter tuning process 1226 can be performed based on the training results 1224 to tune one or more hyperparameters of the bed group census forecasting models for the bed group. Furthermore, a multi-model weight optimization process 1228 can be performed to determine the optimal weights for multiple (e.g., two or more) models using one or more optimization techniques (e.g., as discussed with reference to forecasting optimization component 608 and FIG. 6). In another aspect, the machine learning model(s) 1222 can provide validation results 1230 to validate the machine learning model(s) 1220. The validation results 1230 can be employed by an evaluate model process 1232 to evaluate one or more metrics for the machine learning model(s). For example, in some embodiments, the validation results 1230 can be used to generate MSE metrics for the model(s) which in turn can be used for the multi-model weight optimization process 1228 and/or the parameter tunning process 1226.

Figure 13:
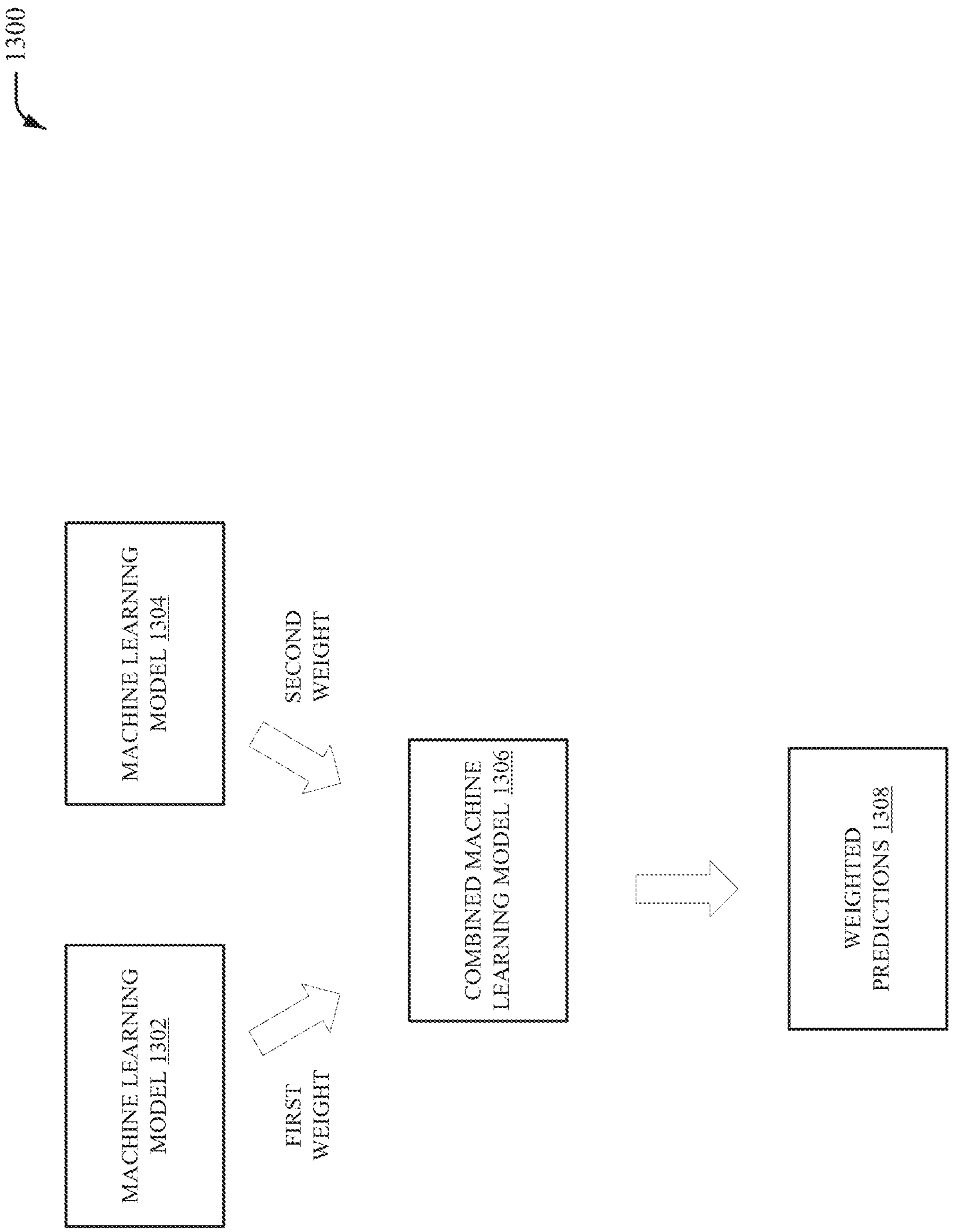
FIG. 13 illustrates an example system associated with combining machine learning models, in accordance with one or more embodiments described herein.

Referring to FIG. 13, there is illustrated a non-limiting implementation of a system 1300 in accordance with various aspects and implementations of this disclosure. Repetitive description of like elements employed in other embodiments described herein is omitted for sake of brevity.

The system 1300 includes a machine learning model 1302 and a machine learning model 1304. In an embodiment, the machine learning model 1302 and the machine learning model 1304 can be the same type of machine learning model. In an alternate embodiment, the machine learning model 1302 and the machine learning model 1304 can be different type of machine learning models. The machine learning model 1302 and the machine learning model 1304 can be employed, for example, to predict patient census data associated with a prediction for a total number of patient identities in a particular inpatient unit and/or bed group during a period of time based on one or more patterns and/or one or more abnormalities associated with current patient flow data 118. In another embodiment, the machine learning model 1302 and/or the machine learning model 1304 can include a plurality of forecast models for different period of time to predict patient census data associated with a prediction for a total number of patient identities in the set of medical inpatient units. For example, the machine learning model 1302 can include a first forecast model for patient census data associated with a first period of time (e.g., a first forecast model for hour 1), a second forecast model for patient census data associated with a second period of time (e.g., a second forecast model for hour 2), a third forecast model for patient census data associated with a third period of time (e.g., a third forecast model for hour 3), a fourth forecast model for patient census data associated with a fourth period of time (e.g., a fourth forecast model for hour 4), a fifth forecast model for patient census data associated with a fifth period of time (e.g., a fifth forecast model for hours 5-8), a sixth forecast model for patient census data associated with a sixth period of time (e.g., a sixth forecast model for hours 9-12), a seventh forecast model for patient census data associated with a seventh period of time (e.g., a seventh forecast model for hours 12-24), and/or an eight forecast model for patient census data associated with an eighth period of time (e.g., an eighth forecast model for hours 25-48). Additionally, the machine learning model 1304 can include a first forecast model for patient census data associated with a first period of time (e.g., a first forecast model for hour 1), a second forecast model for patient census data associated with a second period of time (e.g., a second forecast model for hour 2), a third forecast model for patient census data associated with a third period of time (e.g., a third forecast model for hour 3), a fourth forecast model for patient census data associated with a fourth period of time (e.g., a fourth forecast model for hour 4), a fifth forecast model for patient census data associated with a fifth period of time (e.g., a fifth forecast model for hours 5-8), a sixth forecast model for patient census data associated with a sixth period of time (e.g., a sixth forecast model for hours 9-12), a seventh forecast model for patient census data associated with a seventh period of time (e.g., a seventh forecast model for hours 12-24), and/or an eight forecast model for patient census data associated with an eighth period of time (e.g., an eighth forecast model for hours 25-48).

In an embodiment, different weights can be applied to the machine learning model 1302 and the machine learning model 1304 to generate a combined machine learning model 1306. In various embodiments, the model weights can be determined by the forecasting optimization component 608. For instance, a first weight can be applied to the machine learning model 1302 and a second weight can be applied to the machine learning model 1304. Furthermore, the machine learning model 1302 associated with the first weight can be combined with the machine learning model 1304 associated with the second weight to generate the combined machine learning model 1306. In an aspect, the machine learning model 1302 can be a first machine learning model associated with a first weight and the machine learning model 1304 can be a second machine learning model associated with a second weight that is different than the first weight. In a non-limiting example, the machine learning model 1302 can be associated with a 60% weight and the machine learning model 1304 can be associated with a 40% weight. However, it is to be appreciated that different weights can be applied to the machine learning model 1302 and/or the machine learning model 1304. The combined machine learning model 1306 can provide one or more weighted predictions 1308. For instance, the one or more weighted predictions 1308 can be one or more weighted predictions for the patient census data associated with a prediction for a total number of patient identities the medical inpatient unit and/or bed group during one or more same or different future periods of time. In an example, the combined machine learning model 1306 can provide a weighted first forecast model for patient census data associated with a first period of time (e.g., a first forecast model for hour 1), a weighted second forecast model for patient census data associated with a second period of time (e.g., a second forecast model for hour 2), a weighted third forecast model for patient census data associated with a third period of time (e.g., a third forecast model for hour 3), a weighted fourth forecast model for patient census data associated with a fourth period of time (e.g., a fourth forecast model for hour 4), a weighted fifth forecast model for patient census data associated with a fifth period of time (e.g., a fifth forecast model for hours 5-8), a weighted sixth forecast model for patient census data associated with a sixth period of time (e.g., a sixth forecast model for hours 9-12), a weighted seventh forecast model for patient census data associated with a seventh period of time (e.g., a seventh forecast model for hours 12-24), and/or a weighted eight forecast model for patient census data associated with an eighth period of time (e.g., an eighth forecast model for hours 25-48). In an aspect, the combined machine learning model 1306 and/or the one or more weighted predictions 1308 can provide improved accuracy for predicting patient census data.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 14:
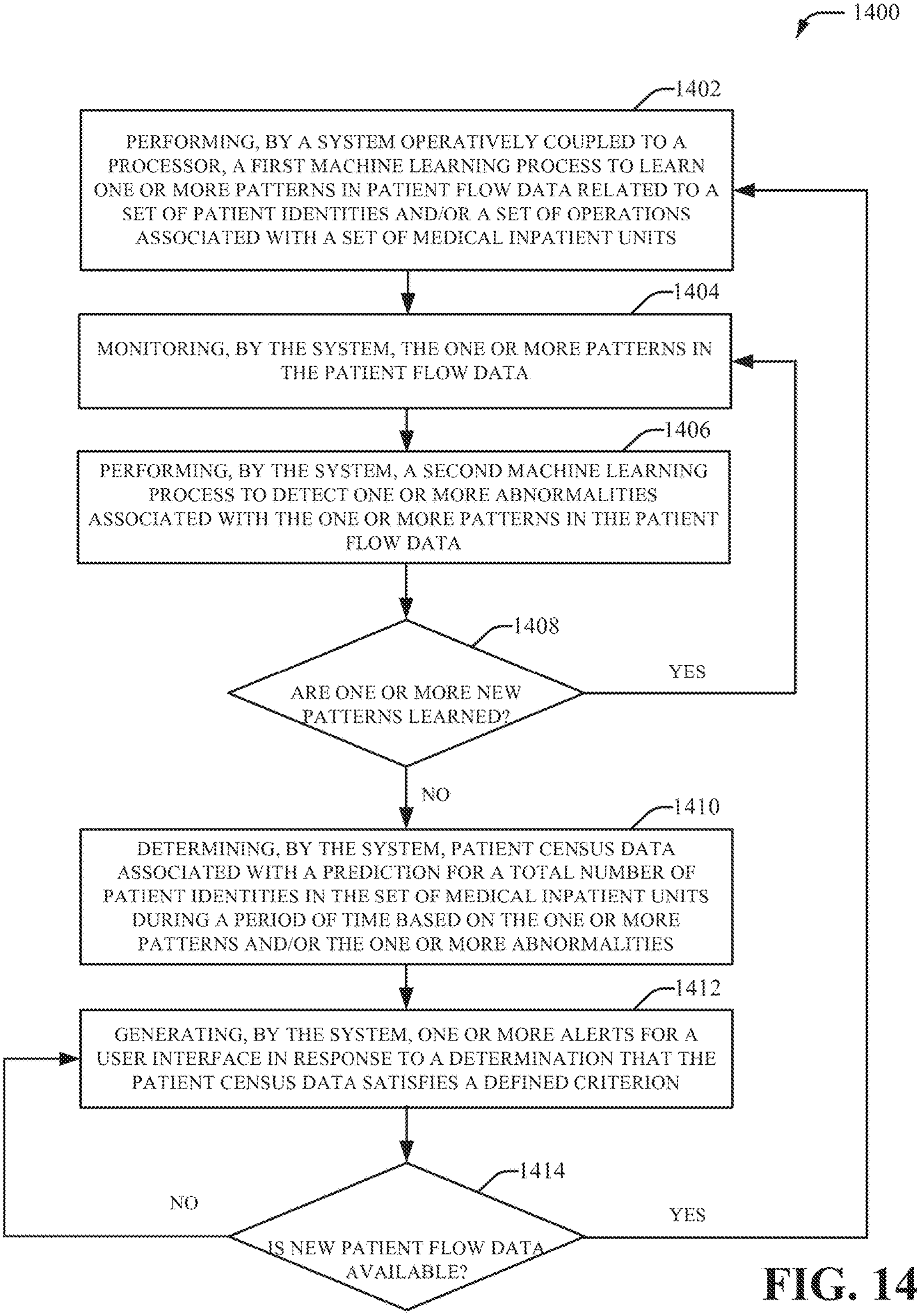
FIG. 14 depicts a flow diagram of an example method for monitoring, predicting and/or alerting for census periods in medical inpatient units, in accordance with one or more embodiments described herein.

FIG. 14 illustrates one or more methodologies and/or flow diagrams in accordance with the disclosed subject matter. For simplicity of explanation, the one or more methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the one or more methodologies in accordance with the disclosed subject matter. In addition, those skilled in the art will understand and appreciate that the one or more methodologies could alternatively be represented as a series of interrelated states via a state diagram or events. Additionally, it should be further appreciated that the one or more methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or storage media.

Referring to FIG. 14, there illustrated is a methodology 1400 for monitoring, predicting and/or alerting for census periods in medical inpatient units, in accordance with one or more embodiments described herein. Repetitive description of like elements employed in other embodiments described herein is omitted for sake of brevity.

As an example, the methodology 1400 can be utilized in various applications, such as, but not limited to, healthcare systems, medical systems, hospital systems, medical device systems, electronic health record systems, electronic medical record systems, forecasting systems, adaptive learning systems, automated learning engine systems, alerting engine systems, machine learning systems, artificial intelligence systems, neural network systems, industrial systems, aviation systems, manufacturing systems, factory systems, energy management systems, power grid systems, water supply systems, transportation systems, refinery systems, media systems, research systems, financial systems, data-driven prognostics systems, network systems, computer network systems, communication systems, router systems, server systems, high availability server systems (e.g., Telecom server systems), Web server systems, file server systems, data server systems, disk array systems, powered insertion board systems, cloud-based systems, and the like. In one example, the system 100 can be associated with a PaaS and/or a medical data management system, etc. At 1402, a first machine learning process is performed, by a system operatively coupled to a processor (e.g., by patient flow component 102), to learn one or more patterns in patient flow data related to a set of patient identities and/or a set of operations associated with a set of medical inpatient units. Additionally, or alternatively, the first machine learning process can determine one or more rules associated with the patient flow data. Additionally, or alternatively, the first machine learning process can determine one or more relationships among the set of medical inpatient units. In an embodiment, principles of artificial intelligence can be employed to facilitate learning one or more patterns in the patient flow data, determining one or more rules associated with the patient flow data, and/or determining one or more relationships among the set of medical inpatient units. For example, one or more machine learning techniques can be employed to facilitate learning one or more patterns in the patient flow data, determining one or more rules associated with the patient flow data, and/or determining one or more relationships among the set of medical inpatient units. The set of medical inpatient units can include one or more medical inpatient units. A medical inpatient unit from the set of medical inpatient units can be, for example, a hospital unit configured to provide one or more medical services to a group of patients. Furthermore, a medical inpatient unit from the set of medical inpatient units can be associated with a location (e.g., a physical location) within a hospital or a group of hospitals. The patient flow data can include medical data, sensor data, process data (e.g., process log data), monitoring data, maintenance data, parameter data, measurement data, performance data, textual data, audio data, image data, video data, machine data, asset data, equipment data, medical device data, meter data, real-time data, historical data and/or other data. Furthermore, the patient flow data can be encoded data, processed data and/or raw data.

In certain embodiments, the patient flow data can include patient data associated with a set of medical inpatient units. The patient data can be, for example, real-time patient data associated with a set of medical inpatient units. The patient data can be associated with one or more patients. In an aspect, the patient data can be generated by one or more devices and/or one or more equipment located within the set of medical inpatient units. For example, the patient data can be generated by one or more medical devices, one or more medical equipment, one or more sensors, one or more mobile devices, one or more computers, one or more tablet computers, and/or one or more other devices. Furthermore, the one or more devices and/or one or more equipment located within the set of medical inpatient units can be one or more network-connected devices and/or one or more network-connected equipment. In another aspect, the patient data can be obtained from one or more medical logs. For example, the patient data can be obtained from one or more electronic medical records. Additionally, or alternatively, the patient flow data can include operations data associated with the set of medical inpatient units. The operations data can be associated with one or more operational processes associated with the set of medical inpatient units. For instance, the operations data can include status information associated with one or more medical procedures performed within the set of medical inpatient units, time information associated with one or more medical procedures performed within the set of medical inpatient units, statistical information associated with one or more medical procedures performed within the set of medical inpatient units, efficiency information associated with one or more medical procedures performed within the set of medical inpatient units, and/or other information associated with one or more medical procedures performed within the set of medical inpatient units. The operations data can additionally or alternatively include information associated with medical staff within the set of medical inpatient units. For example, the operations data can include status information associated with medical staff within the set of medical inpatient units, time information associated with medical staff within the set of medical inpatient units, location information associated with medical staff within the set of medical inpatient units, statistical information associated with medical staff within the set of medical inpatient units, efficiency information associated with medical staff within the set of medical inpatient units, and/or other information associated with medical staff within the set of medical inpatient units. Additionally, or alternatively, the patient flow data can include resource data associated with the set of medical inpatient units. The resource data can be associated with one or more resources utilized within the set of medical inpatient units. For example, the resource data can include medication information utilized within the set of medical inpatient units, medical supplies information utilized within the set of medical inpatient units, medical equipment information utilized within the set of medical inpatient units, and/or other resource information utilized within the set of medical inpatient units. In another embodiment, the patient flow data can provide aggregated information associated with the patient data, the operations data and/or the resource data. Therefore, the patient flow data can provide information associated with patient flow throughout the set of medical inpatient units. For example, the patient flow data can provide real-time patient flow information throughout the set of medical inpatient units.

At 1404, the one or more patterns in the patient flow data are monitored, by the system (e.g., by monitoring engine component 104). Additionally, or alternatively, the one or more rules associated with the patient flow data 118 can be monitored. Additionally, or alternatively, the one or more relationships among the set of medical inpatient units can be monitored. In an embodiment, principles of artificial intelligence can be employed to facilitate monitoring the one or more patterns in the patient flow data and/or generating the one or more abnormalities associated with the one or more patterns in the patient flow data. For example, one or more machine learning techniques can be employed to facilitate monitoring the one or more patterns in the patient flow data and/or generating the one or more abnormalities associated with the one or more patterns in the patient flow data.

At 1406, a second machine learning process is performed, by the system (e.g., by monitoring engine component 104), to detect one or more abnormalities associated with the one or more patterns in the patient flow data. The one or more abnormalities associated with the one or more patterns in the patient flow data can be one or more anomalies associated with the one or more patterns in the patient flow data. For instance, the one or more abnormalities associated with the one or more patterns in the patient flow data can be unique behavior and/or unique characteristics associated with the one or more patterns in the patient flow data. In an example, an abnormality associated with the one or more patterns in the patient flow data can be a change or a difference with respect to one or more other predetermined patterns in the patient flow data. In certain embodiments, the one or more patterns in the patient flow data can be compared to one or more other patterns (e.g., one or more predetermined patterns) to facilitate detection of the one or more abnormalities. In an embodiment, the one or more abnormalities associated with the one or more patterns in the patient flow data can predict and/or indicate an event associated with the one or more patterns in the patient flow data. A match between a pattern and another pattern can be, for example, approximately an exact match. Alternatively, a match between a pattern and another pattern can be, for example, a fuzzy match. In certain embodiments, similarity between a pattern and another pattern can be computed based on one or more pattern recognition techniques, one or more statistical techniques, and/or one or more artificial intelligence techniques. In another embodiment, similarity between a pattern and another pattern can be computed based on a distance metric. For example, similarity between a pattern and another pattern can be computed based on a Hamming distance. In another example, similarity between a pattern and another pattern can be computed based on based on a Jaccard distance.

At 1408, it is determined whether one or more new patterns are learned. If yes, the methodology 1400 returns to 1404. If no, the methodology 1400 proceeds to 1410.

At 1410, patient census data associated with a prediction for a total number of patient identities in the set of medical inpatient units during a period of time is determined, by the system (e.g., by patient census component 106), based on the one or more patterns and/or the one or more abnormalities. For example, patient census data can provide a prediction for a total number of patients that will utilize one or more medical inpatient units from the set of medical inpatient units during a future period of time. The patient census data can additionally or alternatively provide one or more predicted emerging patterns in the set of medical inpatient units during the period of time (e.g., the future period of time).

At 1412, one or more alerts for a user interface is generated, by the system (e.g., by alert component 108), in response to a determination that the patient census data satisfies a defined criterion. In an embodiment, the one or more alerts can be generated in response to a determination that the patient census data exceeds a defined threshold. For example, the one or more alerts can be generated in response to a determination that the patient census data indicates an extreme census period for one or more medical inpatient units from the set of medical inpatient units. In an embodiment, the one or more alerts can be provided to a display device associated with the user interface such as, for example, a mobile device, a mobile application for a mobile device, a computer, a table computer, a wall display, a monitor and/or another type of display device. In certain embodiments, the one or more alerts can alter a graphical element and/or a graphical indicator for the user interface. For example, the one or more alerts can alter a color of a graphical element associated with the user interface. In certain embodiments, the one or more alerts can provide an indicator associated with one or more emerging census patterns in the set of medical inpatient units. In an embodiment, the patient census data (e.g., the one or more alerts associated with the patient census data) can be outputted in a human interpretable format via a display device associated with the user interface.

At 1414, it is determined whether new patient flow data is available. If yes, the methodology 1400 returns to 1402. If no, the methodology 1400 returns to 1412. In certain embodiments, the methodology 1400 can additionally or alternatively include tuning one or more parameters for a machine learning model associated with the first machine learning process and/or the second machine learning process based on an evaluation of the patient census data.

Figure 15:
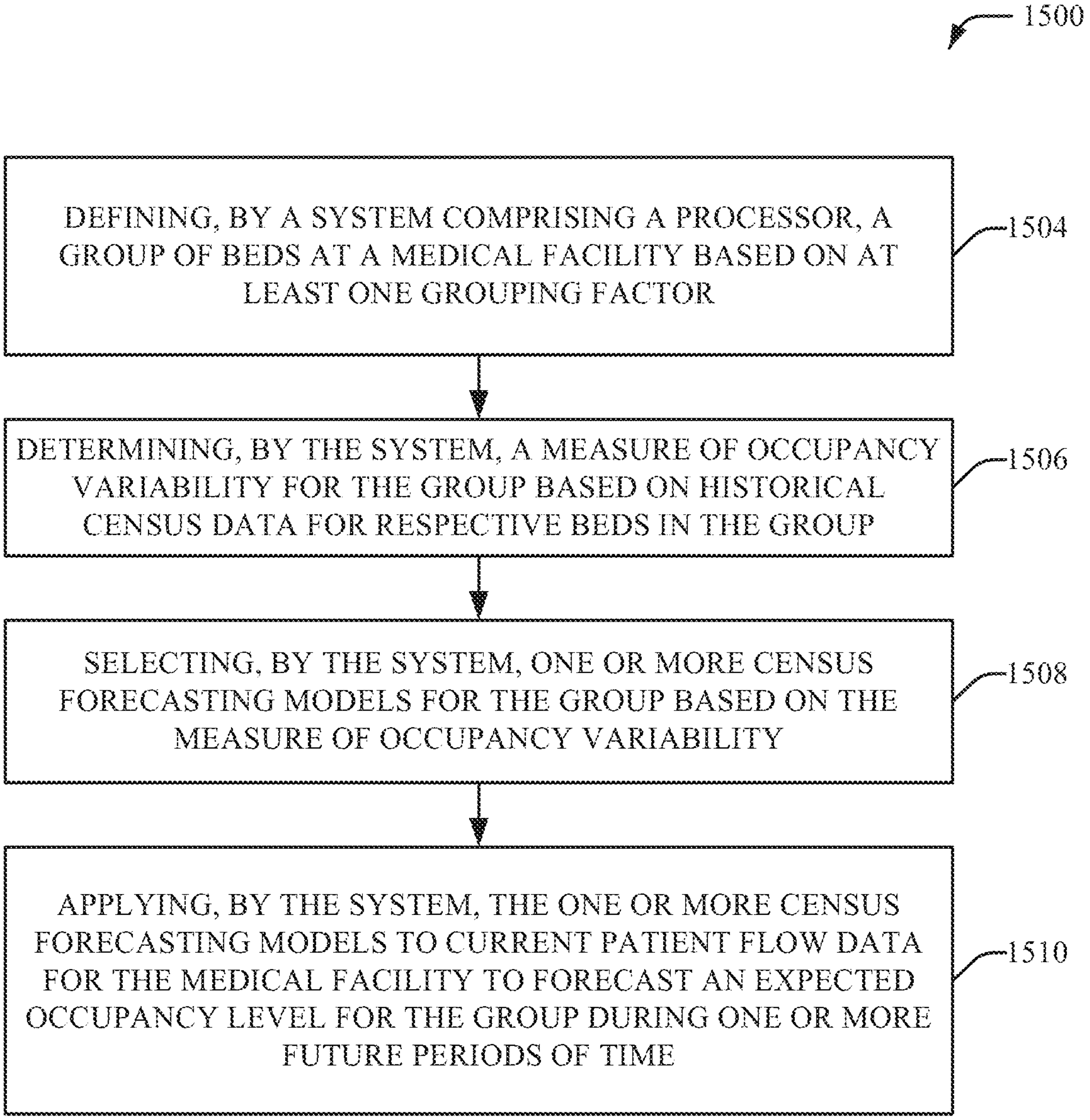
FIG. 15 depicts a flow diagram of an example method for forecasting census data for a grouping of beds at a medical facility, in accordance with one or more embodiments described herein.

FIG. 15 depicts a flow diagram of an example method 1500 for forecasting census data for a grouping of beds at a medical facility, in accordance with one or more embodiments described herein. In accordance with method 1500, at 1502, a system comprising a processor, may define a group of beds at a medical facility based on at least one grouping factor (e.g., via the grouping component 602). At 1504, the system may determine a measure of occupancy variability for the group based on historical census data for respective beds in the group (e.g., via the group stability component 604). At 1506, the system may select one or more census forecasting models for the group based on the measure of occupancy variability (e.g., via the model selection component 606). At 1508, the system may apply the one or more census forecasting models to current patient flow data for the medical facility to forecast an expected occupancy level for the group during one or more future periods of time (e.g., via the patient census component 106).

Figure 16:
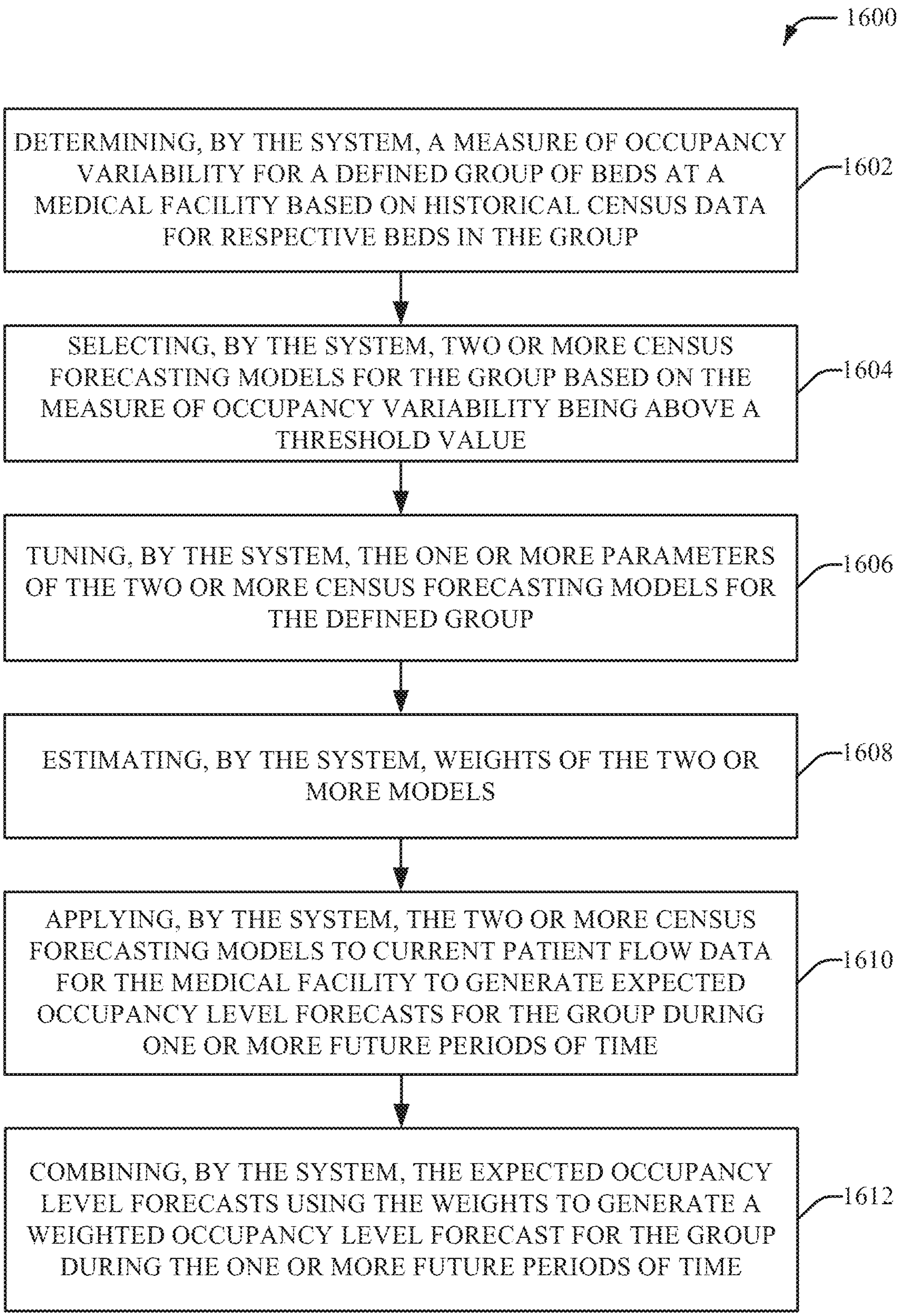
FIG. 16 depicts a flow diagram of another example method for forecasting census data for a grouping of beds at a medical facility, in accordance with one or more embodiments described herein.

FIG. 16 depicts a flow diagram of another example method 1600 for forecasting census data for a grouping of beds at a medical facility, in accordance with one or more embodiments described herein. In accordance with method 1600, at 1602, a system comprising a processor, may determine a measure of occupancy variability for a defined group of beds at a medical facility based on historical census data for respective beds in the group (e.g., via the group stability component 604). At 1606, the system may select two or more census forecasting models for the group based on the measure of occupancy variability being above a threshold value (e.g., via the model selection component 606). For example, the model selection component 606 may be configured to select two or more ML models as opposed to a single model when the measure of variability is high. At 1606, the system may tune one or more parameters of the two or more census forecasting models for the defined group (e.g., via the forecasting optimization component 606). At 1608, the system may estimate weights of the two or more models (e.g., via the forecasting optimization component 606). At 1610, the system may apply the two or more census forecasting models to current patient flow data for the medical facility to generate expected occupancy level forecasts for the group during one or more future periods of time (e.g., via the patient census component 106). At 1612, the system may combine the expected occupancy level forecasts using the weights to generate a weighted occupancy level forecast for the group during one or more future periods of time (e.g., via the patient census component 106 and/or the forecasting optimization component 606).

Figure 17:
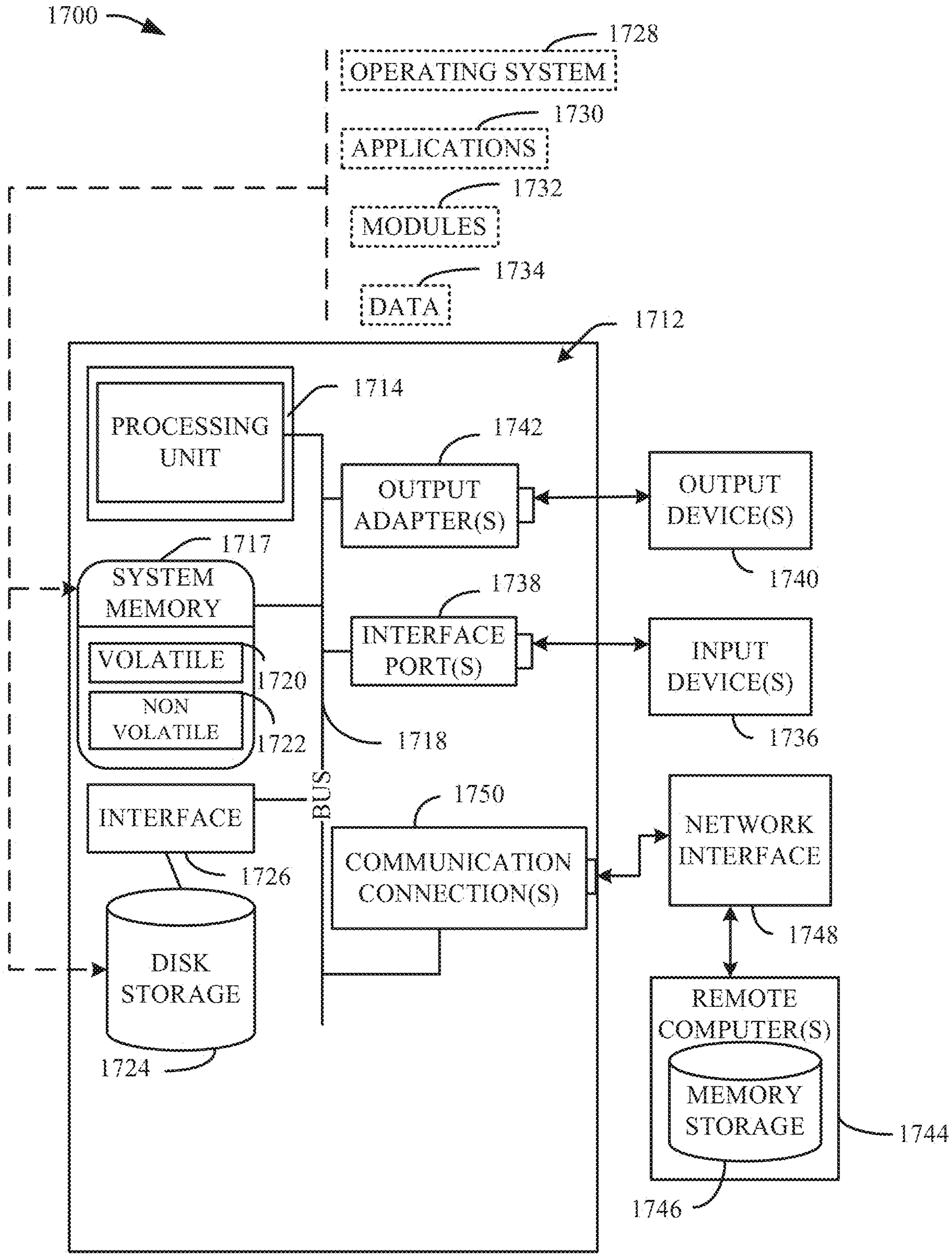
FIG. 17 is a schematic block diagram illustrating a suitable operating environment.
Figure 18:
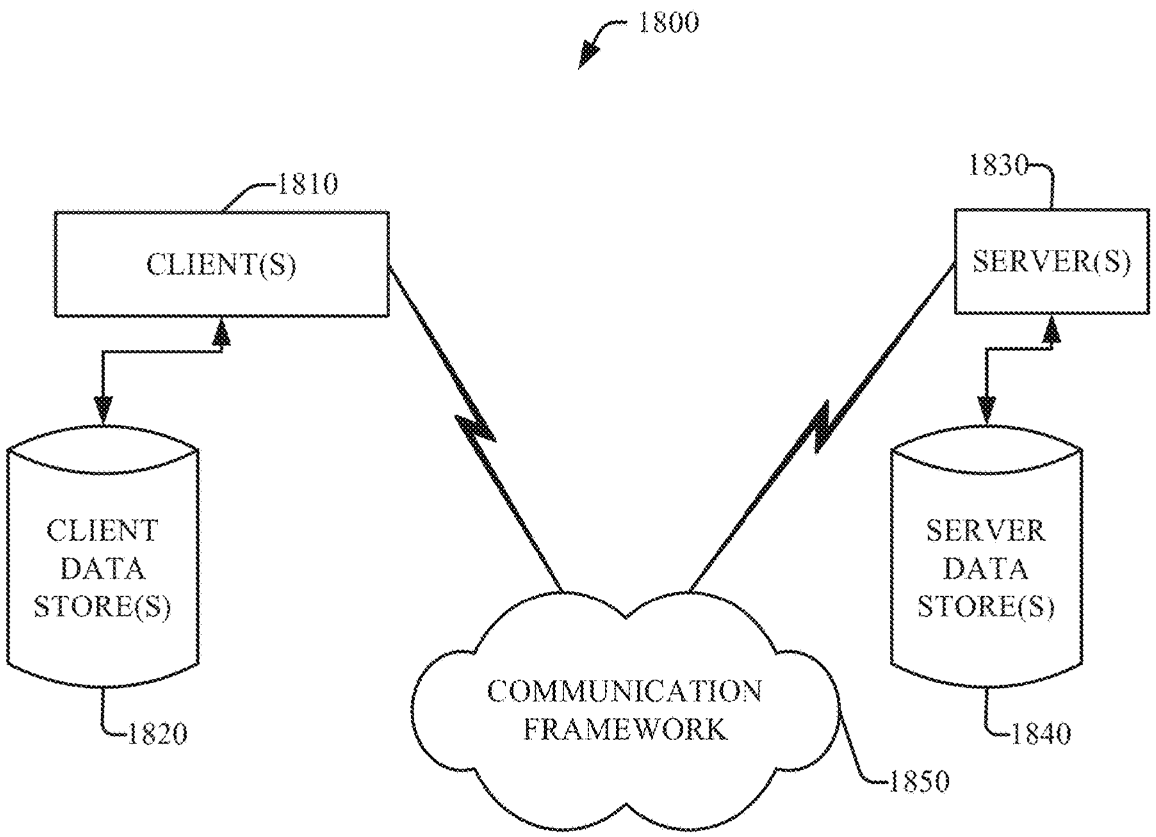
FIG. 18 is a schematic block diagram of a sample-computing environment.

In order to provide a context for the various aspects of the disclosed subject matter, FIGS. 17 and 18 as well as the following discussion are intended to provide a brief, general description of a suitable environment in which the various aspects of the disclosed subject matter may be implemented.

With reference to FIG. 17, a suitable environment 1700 for implementing various aspects of this disclosure includes a computer 1712. The computer 1712 includes a processing unit 1714, a system memory 1716, and a system bus 1718. The system bus 1718 couples system components including, but not limited to, the system memory 1716 to the processing unit 1714. The processing unit 1714 can be any of various available processors. Dual microprocessors and other multiprocessor architectures also can be employed as the processing unit 1714.

The system bus 1718 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1716 includes volatile memory 1720 and nonvolatile memory 1722. The basic input/output system (BIOS), containing the basic routines to transfer information between elements within the computer 1712, such as during start-up, is stored in nonvolatile memory 1722. By way of illustration, and not limitation, nonvolatile memory 1722 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1720 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1712 also includes removable/non-removable, volatile/non-volatile computer storage media. FIG. 17 illustrates, for example, a disk storage 1724. Disk storage 1724 includes, but is not limited to, devices like a magnetic disk drive, floppy disk drive, tape drive, Jaz drive, Zip drive, LS-170 drive, flash memory card, or memory stick. The disk storage 1724 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1724 to the system bus 1718, a removable or non-removable interface is typically used, such as interface 1726.

FIG. 17 also depicts software that acts as an intermediary between users and the basic computer resources described in the suitable operating environment 1700. Such software includes, for example, an operating system 1728. Operating system 1728, which can be stored on disk storage 1724, acts to control and allocate resources of the computer system 1712. System applications 1730 take advantage of the management of resources by operating system 1728 through program modules 1732 and program data 1734, e.g., stored either in system memory 1716 or on disk storage 1724. It is to be appreciated that this disclosure can be implemented with various operating systems or combinations of operating systems.

A user enters commands or information into the computer 1712 through input device(s) 1736. Input devices 1736 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1714 through the system bus 1718 via interface port(s) 1738. Interface port(s) 1738 include, for example, a serial port, a parallel port, a game port, and a universal serial bus (USB). Output device(s) 1740 use some of the same type of ports as input device(s) 1736. Thus, for example, a USB port may be used to provide input to computer 1712, and to output information from computer 1712 to an output device 1740. Output adapter 1742 is provided to illustrate that there are some output devices 1740 like monitors, speakers, and printers, among other output devices 1740, which require special adapters. The output adapters 1742 include, by way of illustration and not limitation, video and sound cards that provide a means of connection between the output device 1740 and the system bus 1718. It should be noted that other devices and/or systems of devices provide both input and output capabilities such as remote computer(s) 1744.

Computer 1712 can operate in a networked environment using logical connections to one or more remote computers, such as remote computer(s) 1744. The remote computer(s) 1744 can be a personal computer, a server, a router, a network PC, a workstation, a microprocessor based appliance, a peer device or other common network node and the like, and typically includes many or all of the elements described relative to computer 1712. For purposes of brevity, only a memory storage device 1746 is illustrated with remote computer(s) 1744. Remote computer(s) 1744 is logically connected to computer 1712 through a network interface 1748 and then physically connected via communication connection 1750. Network interface 1748 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1750 refers to the hardware/software employed to connect the network interface 1748 to the bus 1718. While communication connection 1750 is shown for illustrative clarity inside computer 1712, it can also be external to computer 1712. The hardware/software necessary for connection to the network interface 1748 includes, for exemplary purposes only, internal and external technologies such as, modems including regular telephone grade modems, cable modems and DSL modems, ISDN adapters, and Ethernet cards.

FIG. 18 is a schematic block diagram of a sample-computing environment 1800 with which the subject matter of this disclosure can interact. The system 1800 includes one or more client(s) 1810. The client(s) 1810 can be hardware and/or software (e.g., threads, processes, computing devices). The system 1800 also includes one or more server(s) 1830. Thus, system 1800 can correspond to a two-tier client server model or a multi-tier model (e.g., client, middle tier server, data server), amongst other models. The server(s) 1830 can also be hardware and/or software (e.g., threads, processes, computing devices). The servers 1830 can house threads to perform transformations by employing this disclosure, for example. One possible communication between a client 1810 and a server 1830 may be in the form of a data packet transmitted between two or more computer processes.

The system 1800 includes a communication framework 1850 that can be employed to facilitate communications between the client(s) 1810 and the server(s) 1830. The client(s) 1810 are operatively connected to one or more client data store(s) 1820 that can be employed to store information local to the client(s) 1810. Similarly, the server(s) 1830 are operatively connected to one or more server data store(s) 1840 that can be employed to store information local to the servers 1830.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A system, comprising:

a memory that stores computer executable components; and a processor that executes the computer executable components stored in the memory, wherein the computer executable components comprise:

a training component that performs one or more machine learning processes to learn patterns in historical census data and historical patient flow data related to a flow of patients in and out of respective beds in a group at a medical facility, wherein the training component generates one or more census forecasting models based on the patterns, wherein the historical patient flow data comprises patient journey data tracked for a plurality of patients regarding their journeys at the medical facility, the patient journey data comprising information regarding workflow events, condition of the patients, operations of the medical facility and temporal relationships between the workflow events, the conditions of the patients and the operations, or a combination thereof, wherein the training component models the patient journey data as a heterogeneous graph comprising nodes representing patient attributes and workflow events and arcs representing relationships between the patient attributes and the workflow events, wherein the one or more machine learning processes learn the patterns from the heterogeneous graph;

a patient census component that applies the one or more census forecasting models to current patient flow data for the medical facility to forecast an expected occupancy level for the group during one or more future periods of time, wherein a forecasting optimization component tunes one or more parameters of the one or more census forecasting models for the group prior to application by the patient census component to the current patient flow data to forecast the expected occupancy level for the group; and an alert component that provides an alert to a device associated with the medical facility in response to the expected occupancy level meeting a threshold value.

2. The system of claim 1, wherein a number and type of the one or more census forecasting models is selected by the training component to vary as a function of a measure of occupancy variability.

3. The system of claim 1, wherein the one or more census forecasting models comprise a plurality of different forecasting models, and wherein the forecasting optimization component estimates weights for the plurality of different forecasting models and combines outputs of the different forecasting models using the weights to forecast the expected occupancy level.

4. The system of claim 3, wherein the forecasting optimization component employ a non-convex optimization technique to estimate the weights.

5. The system of claim 4, wherein the non-convex optimization technique comprises a quadratic programming optimization technique.

6. The system of claim 1, wherein learning comprises employing label propagation to infer bed placement patterns from the heterogenous graphs, and wherein the one or more machine learning processes further comprise extracting features from the heterogenous graphs that are correlated to the bed placement patterns.

7. The system of claim 1, wherein a grouping component defines the group of beds at the medical facility based on at least one grouping factor, wherein the at least one grouping factor comprises a unit grouping factor identifying two or more inpatient units of the medical facility, and wherein the grouping component groups the bed based on association of the beds with the two or more inpatient units.

8. The system of claim 1, wherein a grouping component defines the group of beds at the medical facility based on at least one grouping factor, wherein the at least one grouping factor comprise a service line grouping factor identifying at least one service line at the medical facility and wherein the grouping component groups the bed based on association of the beds with the at least one service line.

9. The system of claim 2, wherein a grouping component defines the group of beds at the medical facility based on at least one grouping factor, wherein the at least one grouping factor comprises a bed attribute shared by the beds in the group and a time period of the one or more future periods of time, and wherein a group stability component determines the measure of occupancy variability for the time period.

10. A method, comprising:

executing, by a system, one or more machine learning processes to learn patterns in historical patient flow data related to a flow of patients in and out of respective beds in a group at a medical facility, wherein the executing comprises generating one or more census forecasting models based on the patterns, wherein the historical patient flow data comprises patient journey data tracked for a plurality of patients regarding their journeys at the medical facility, the patient journey data comprising information regarding workflow events, condition of the patients, operations of the medical facility and temporal relationships between the workflow events, the conditions of the patients and the operations, or a combination thereof, wherein the patient journey data is modeled as a heterogeneous graph comprising nodes representing patient attributes and workflow events and arcs representing relationships between the patient attributes and the workflow events, wherein the one or more machine learning processes learn the patterns from the heterogeneous graph;

selecting, by the system, the one or more census forecasting models for the group based on a measure of occupancy variability;

applying, by the system, the one or more census forecasting models to current patient flow data for the medical facility to forecast an expected occupancy level for the group during one or more future periods of time;

tuning one or more parameters of the one or more census forecasting models for the group prior to application to the current patient flow data to forecast the expected occupancy level for the group; and providing an alert to a device associated with the medical facility in response to the expected occupancy level meeting a threshold value.

11. The method of claim 10, wherein a number and type of the one or more census forecasting models selected varies as a function of the measure of occupancy variability.

12. The method of claim 10, wherein the one or more census forecasting models comprise a plurality of different forecasting models, and wherein the method further comprises:

estimating, by the system, weights for the plurality of different forecasting models; and combining, by the system, outputs of the plurality of different forecasting models using the weights to forecast the expected occupancy level.

13. The method of claim 12, wherein the estimating comprises employing a non-convex optimization technique to estimate the weights.

14. The method of claim 10, further comprising:

training, by the system, the one or more census forecasting models based on historical census data and the historical patient flow data for the medical facility.

15. The method of claim 14, further comprising:

tailoring, by the system, the one or more forecasting models based on the patterns.

16. The method of claim 10, wherein learning comprises employing label propagation to infer bed placement patterns from the heterogenous graphs, and wherein the one or more machine learning processes further comprise extracting features from the heterogenous graphs that are correlated to the bed placement patterns.

17. A non-transitory machine-readable storage medium, comprising executable instructions that, when executed by a processor, facilitate performance of operations, comprising:

executing one or more machine learning processes to learn patterns in historical patient flow data related to a flow of patients in and out of respective beds in a group at a medical facility, wherein the executing comprises generating one or more census forecasting models based on the patterns, wherein the historical patient flow data comprises patient journey data tracked for a plurality of patients regarding their journeys at the medical facility, the patient journey data comprising information regarding workflow events, condition of the patients, operations of the medical facility and temporal relationships between the workflow events, the conditions of the patients and the operations, or a combination thereof, wherein the patient journey data is modeled as a heterogeneous graph comprising nodes representing patient attributes and workflow events and arcs representing relationships between the patient attributes and the workflow events, wherein the one or more machine learning processes learn the patterns from the heterogeneous graph;

selecting the one or more census forecasting models for the group based on a measure of occupancy variability;

applying one or more census forecasting models to current patient flow data for the medical facility to forecast an expected occupancy level for the group during one or more future periods of time;

tuning one or more parameters of the one or more census forecasting models for the group prior to application to the current patient flow data to forecast the expected occupancy level for the group; and providing an alert to a device associated with the medical facility in response to the expected occupancy level meeting a threshold value.

18. The non-transitory machine-readable storage medium of claim 17, wherein a number and type of the one or more census forecasting models selected varies as a function of the measure of occupancy variability.

* * * * *